(12) United States Patent
Pasricha et al.

(10) Patent No.: US 7,863,275 B2
(45) Date of Patent: Jan. 4, 2011

(54) USES OF TETRAHYDROBIOPTERIN AND DERIVATIVES THEREOF

(75) Inventors: Pankaj J. Pasricha, Cupertino, CA (US); Pandu R. R. Gangula, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 185 days.

(21) Appl. No.: 11/978,335

(22) Filed: Oct. 29, 2007

(65) Prior Publication Data

US 2008/0207579 A1 Aug. 28, 2008

Related U.S. Application Data

(60) Provisional application No. 60/855,275, filed on Oct. 30, 2006.

(51) Int. Cl.
*A61K 31/4985* (2006.01)
(52) U.S. Cl. .................................................. 514/250
(58) Field of Classification Search ........................ None
See application file for complete search history.

(56) References Cited

FOREIGN PATENT DOCUMENTS

WO    WO 2005/020902    10/2005

OTHER PUBLICATIONS

Gumaste et al., Digestion, (2008) 78(4): 173-9 (Abstract).*

Shinozaki, K. et al. Abnormal Biopterin Metabolism is a Major Cause of Impaired Endothelium-Dependent Relaxaton Through Nitric Oxide/$O_2$—Imbalance in Insulin-Resistant Rat Aorta: *Diabetes*, 1999, vol. 48, pp. 2437-2445.

Kawano, N. et al. Identification and Localization of Estrogen Receptor α- and β-positive Cells in Adult Male and Female Mouse intestine at Varous Estrogen Levels: *Histochem Cell Biol*, 2004, vol. 121, pp. 399-405.

Knoferl, M. et al. Female Sex Hormones Regulate Macrophage Function After Trauma-Hemorrhage and Prevent Increased Death Rate From Subsequent Sepsis: *Annals of Surgery*, Jan. 2002, vol. 235, No. 1, pp. 105-112.

Dubuquoy, L. et al. Peroxisome Proliferator-Activated Receptor (PPAR) Gamma: a New Target for the Treatment of Inflammatory Bowel Disease, *Gastroenterol Clin Biol.*, 2000, vol. 24 No. 8-9, pp. 719-724.

Papadakis, K.A. et al. Role of Cytokines in the Pathogenesis of Inflammatory Bowel Disease: *Annual Reviews*, Feb. 2000, vol. 51, pp. 289-298.

Micci, M. et al. Neural Stem Cell Transplantation in the Stomach Rescues Gastric Function in Neuronal Nitric Oxide Synthase-Deficient Mice: *Gastroenterology*, 2005, vol. 129, pp. 1817-1824.

* cited by examiner

*Primary Examiner*—Phyllis G. Spivack
(74) *Attorney, Agent, or Firm*—Benjamin Aaron Adler

(57) ABSTRACT

The present invention discloses methods of treating diabetic gastroparesis by administering tetrahydrobiopterin or a derivative thereof.

6 Claims, 8 Drawing Sheets

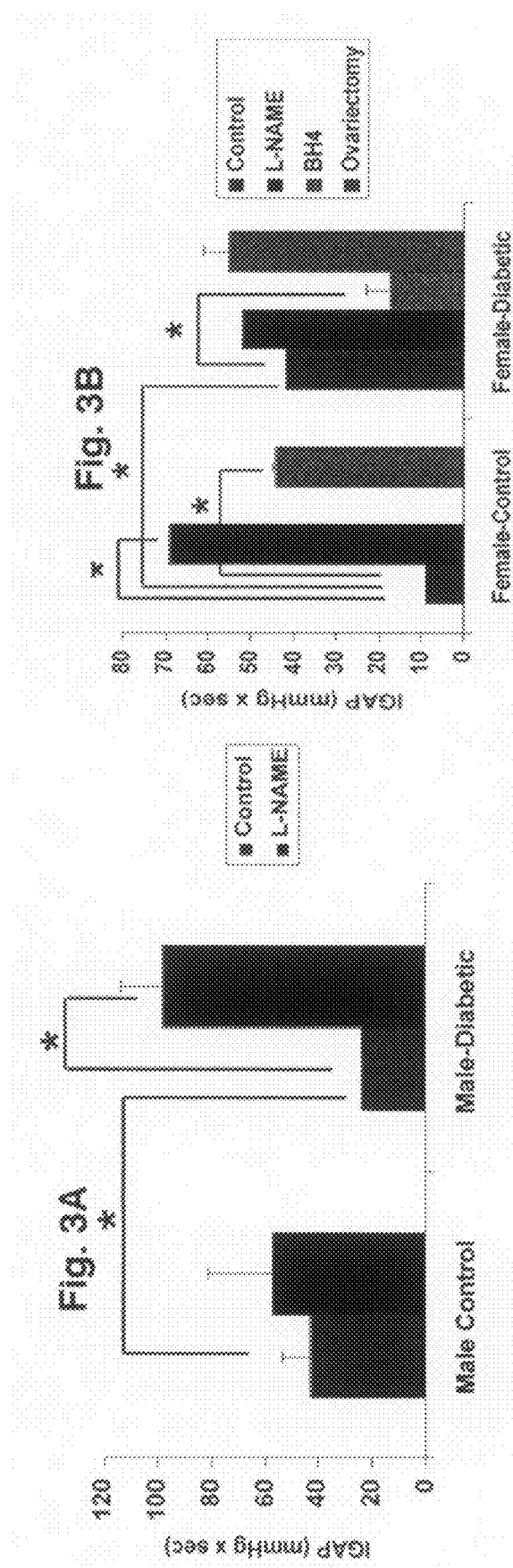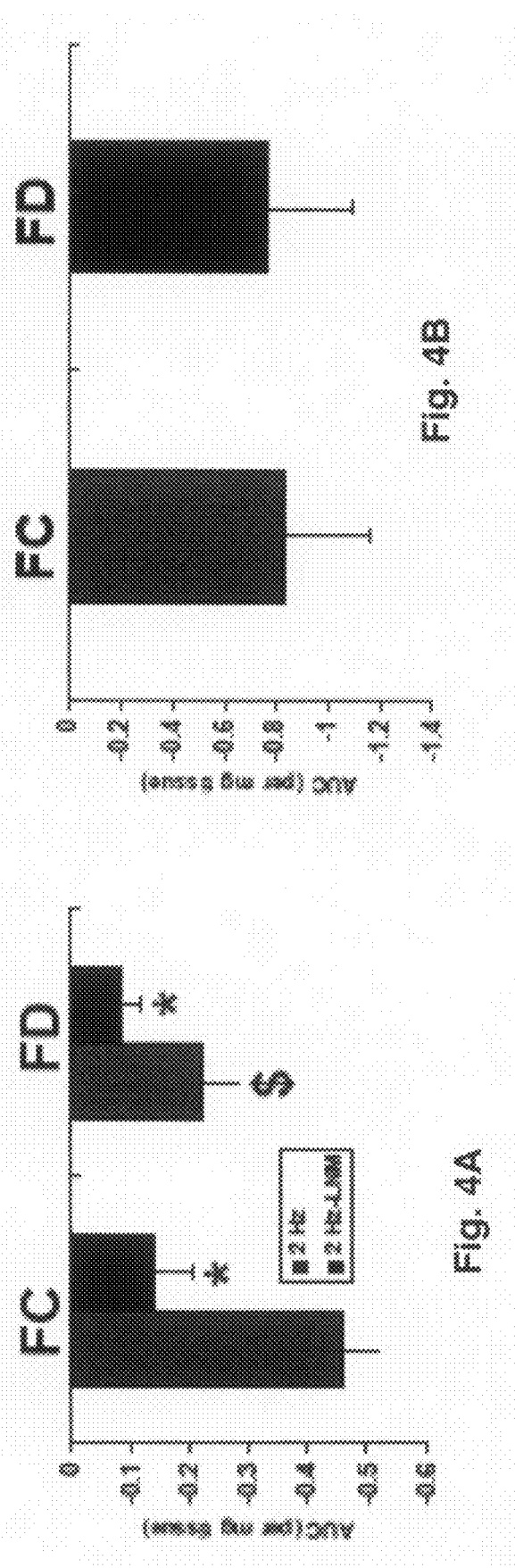

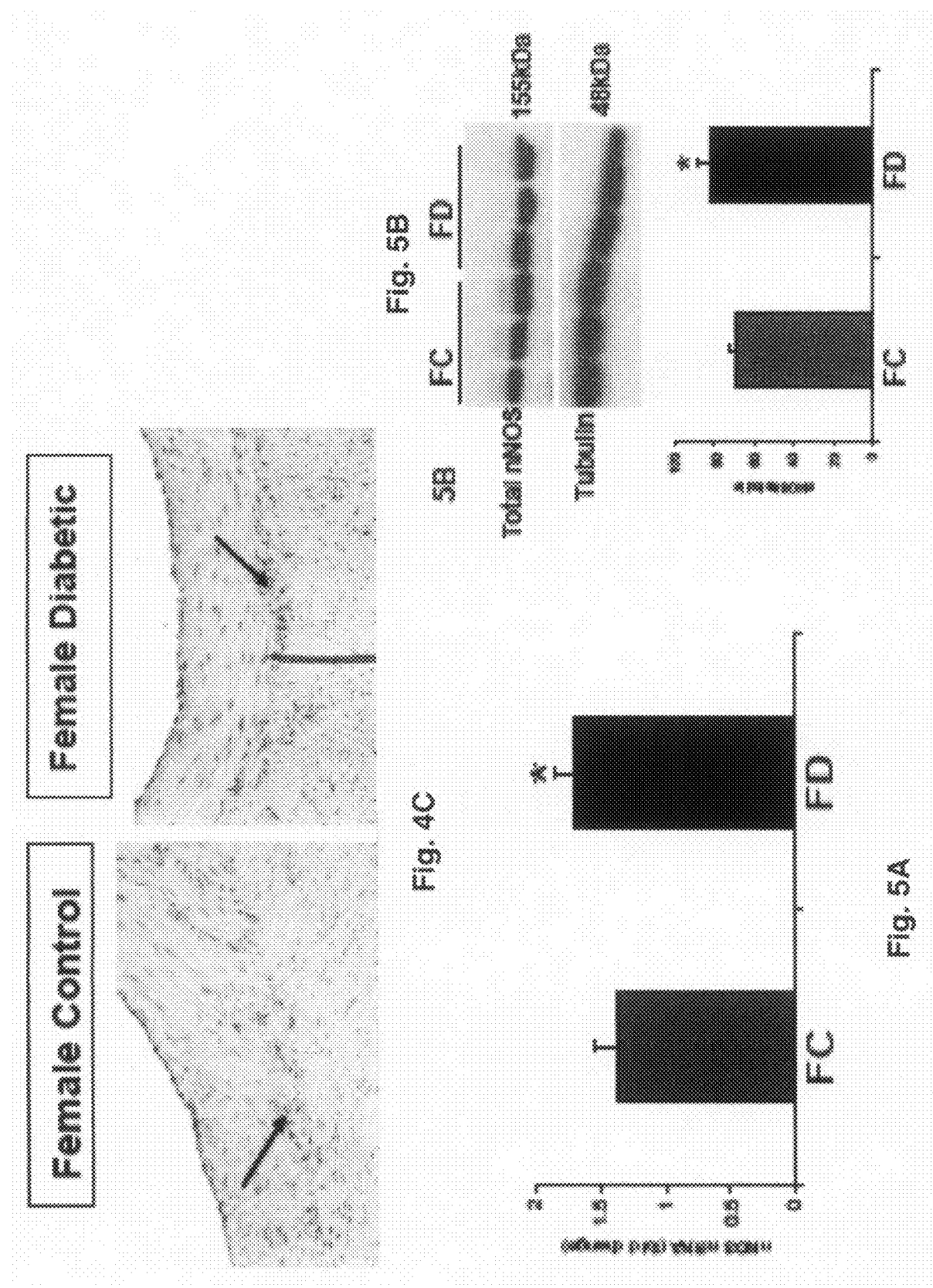

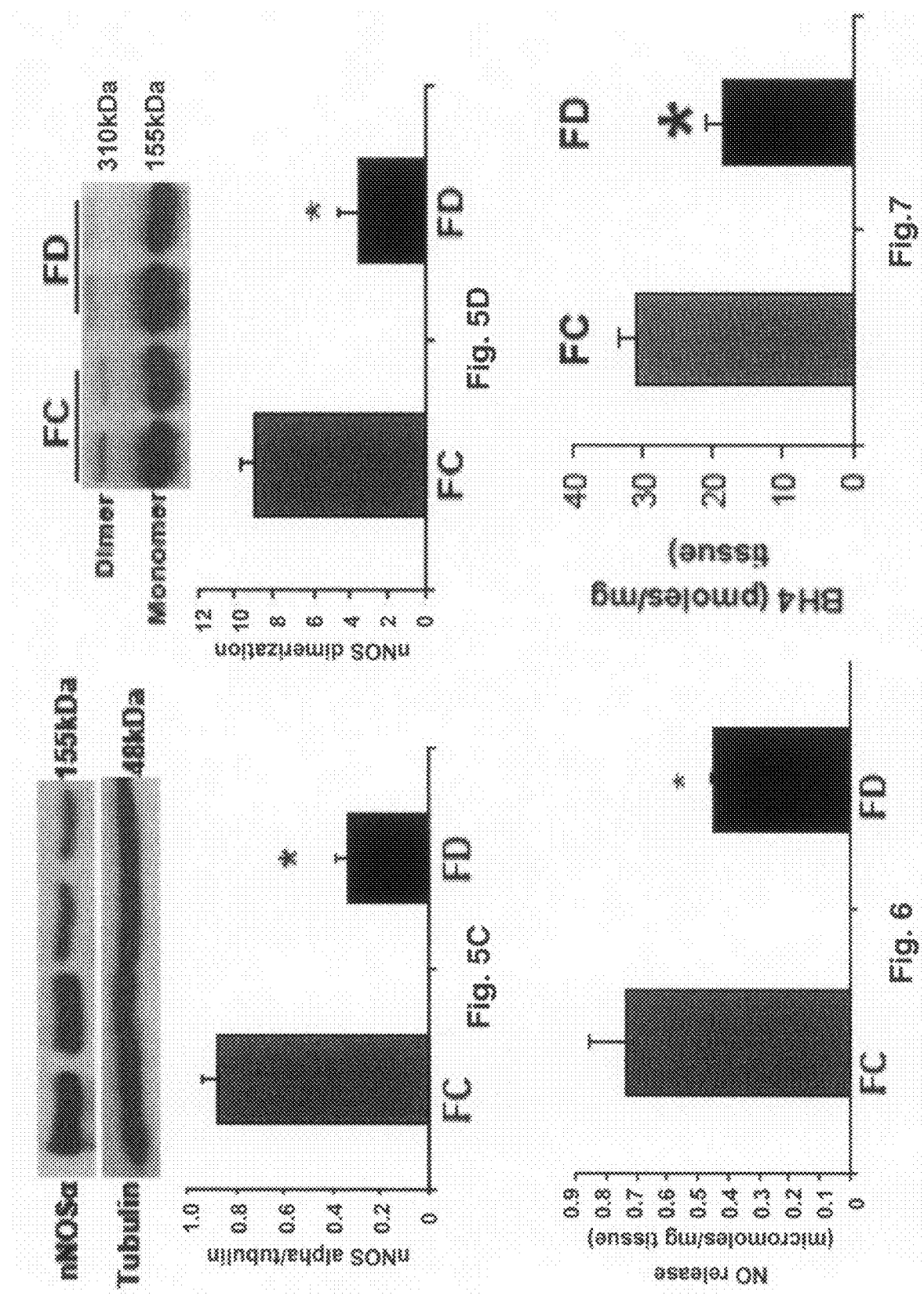

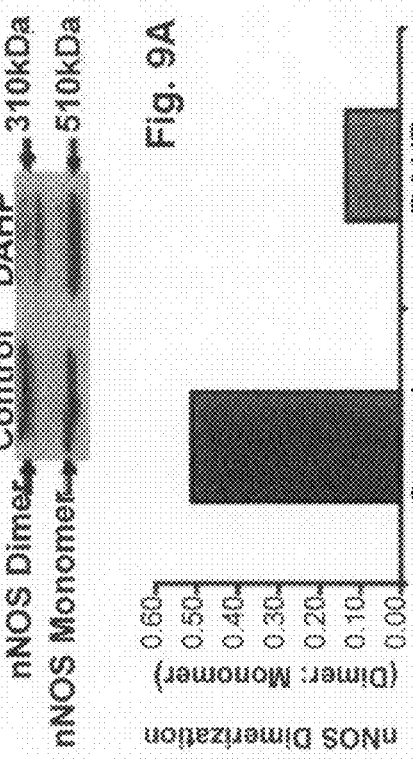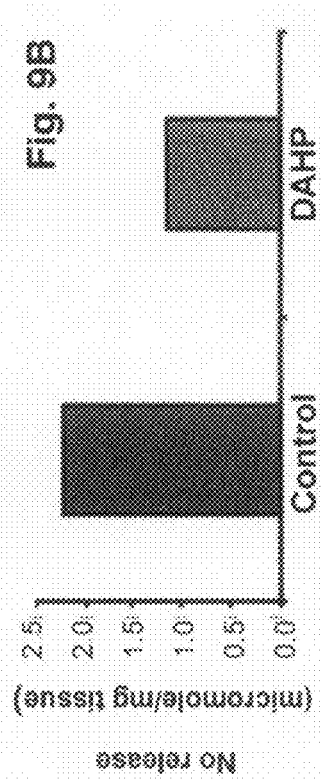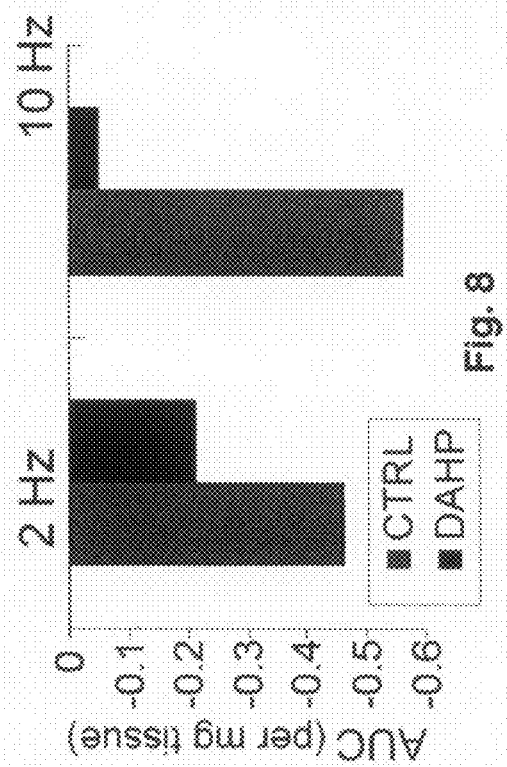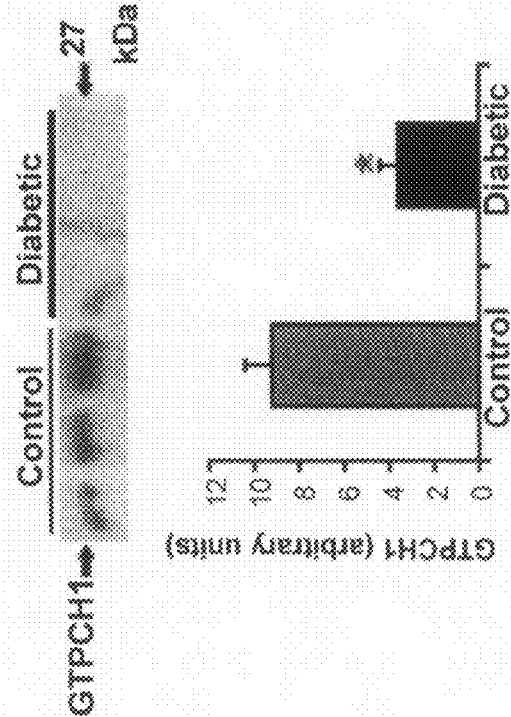
Fig. 9A
Fig. 9B
Fig. 8
Fig. 10

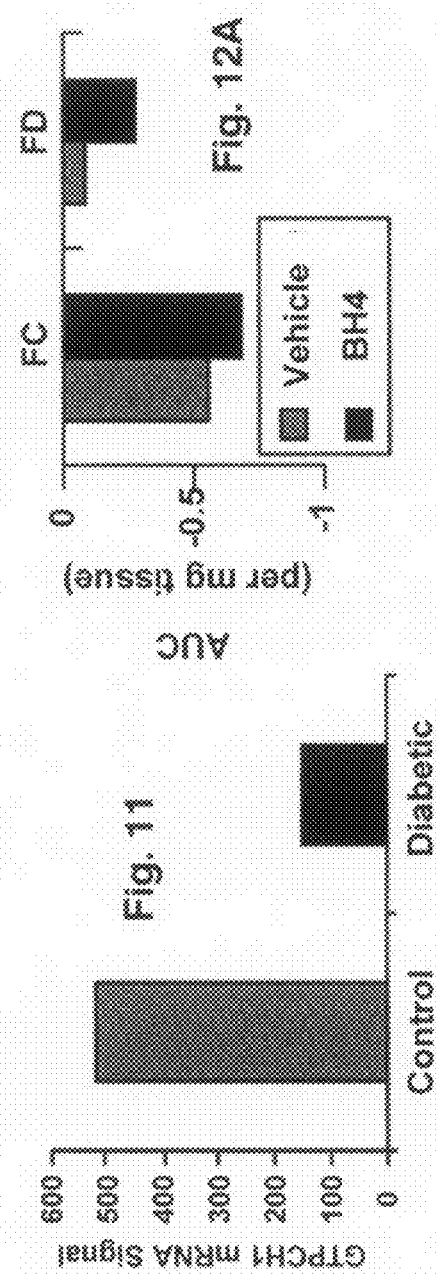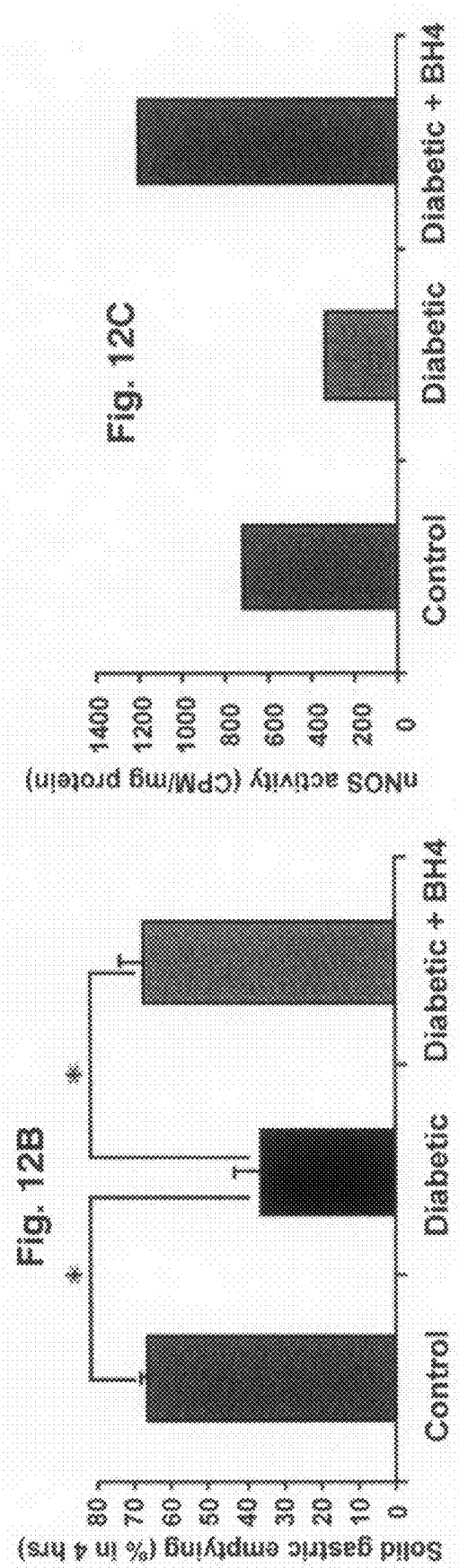

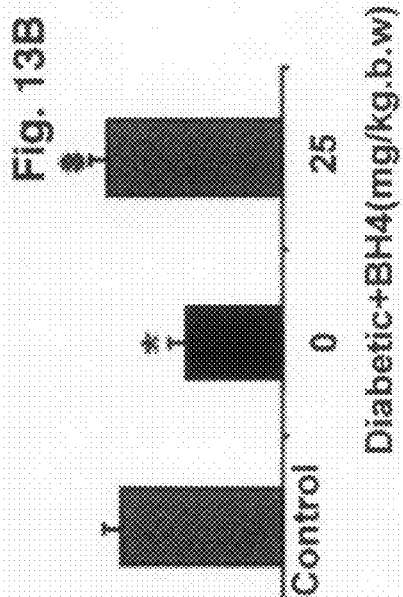
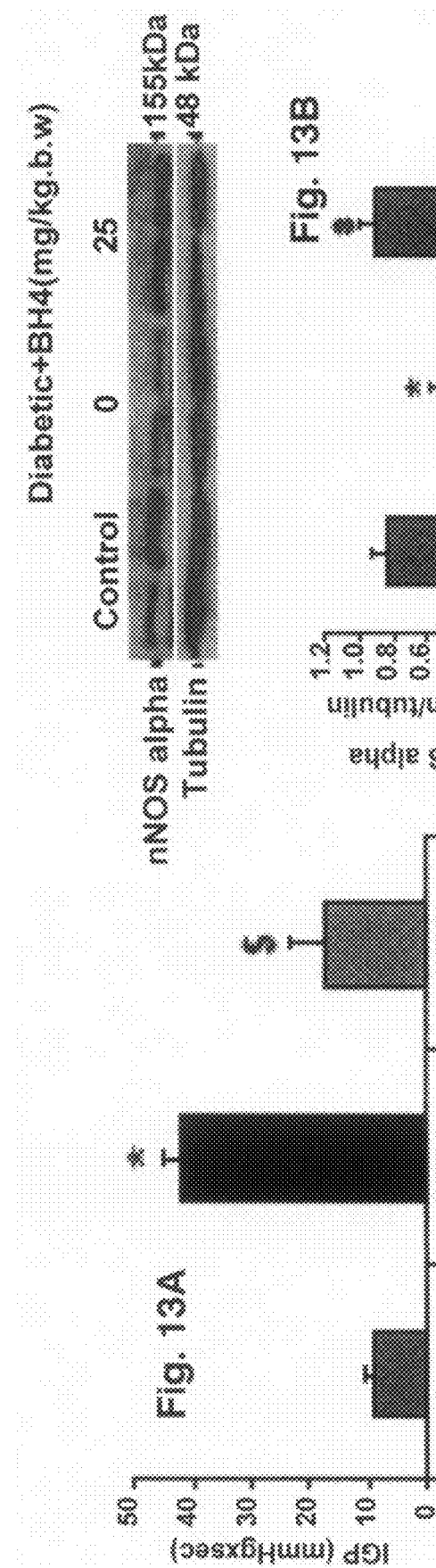
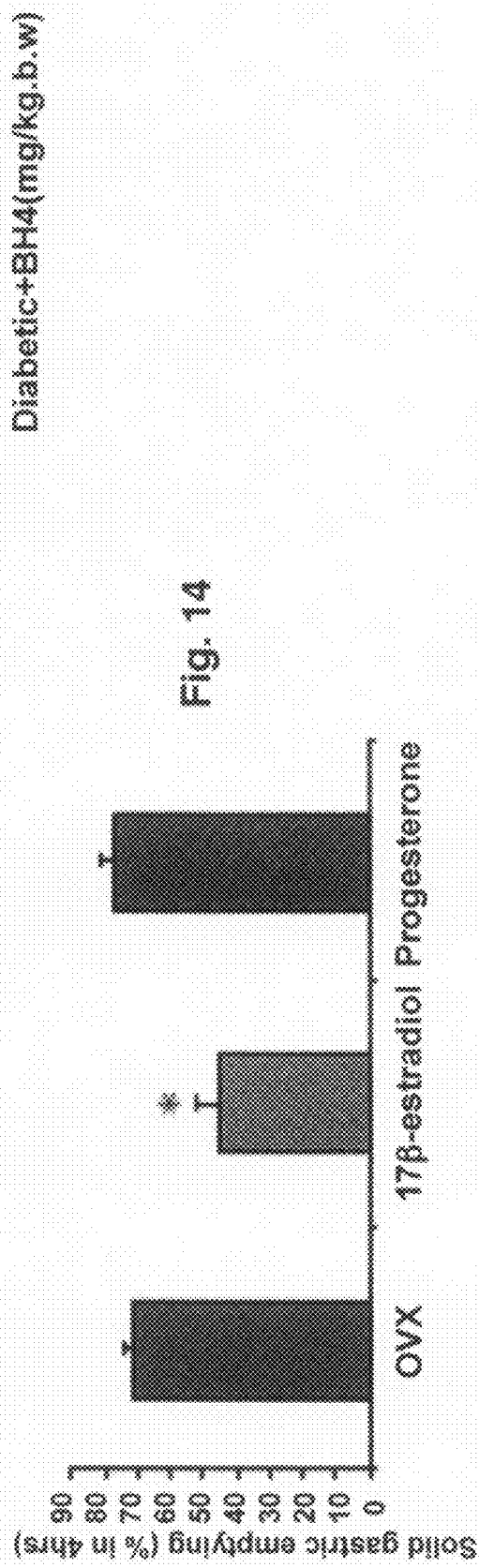
Fig. 13A
Fig. 13B
Fig. 14

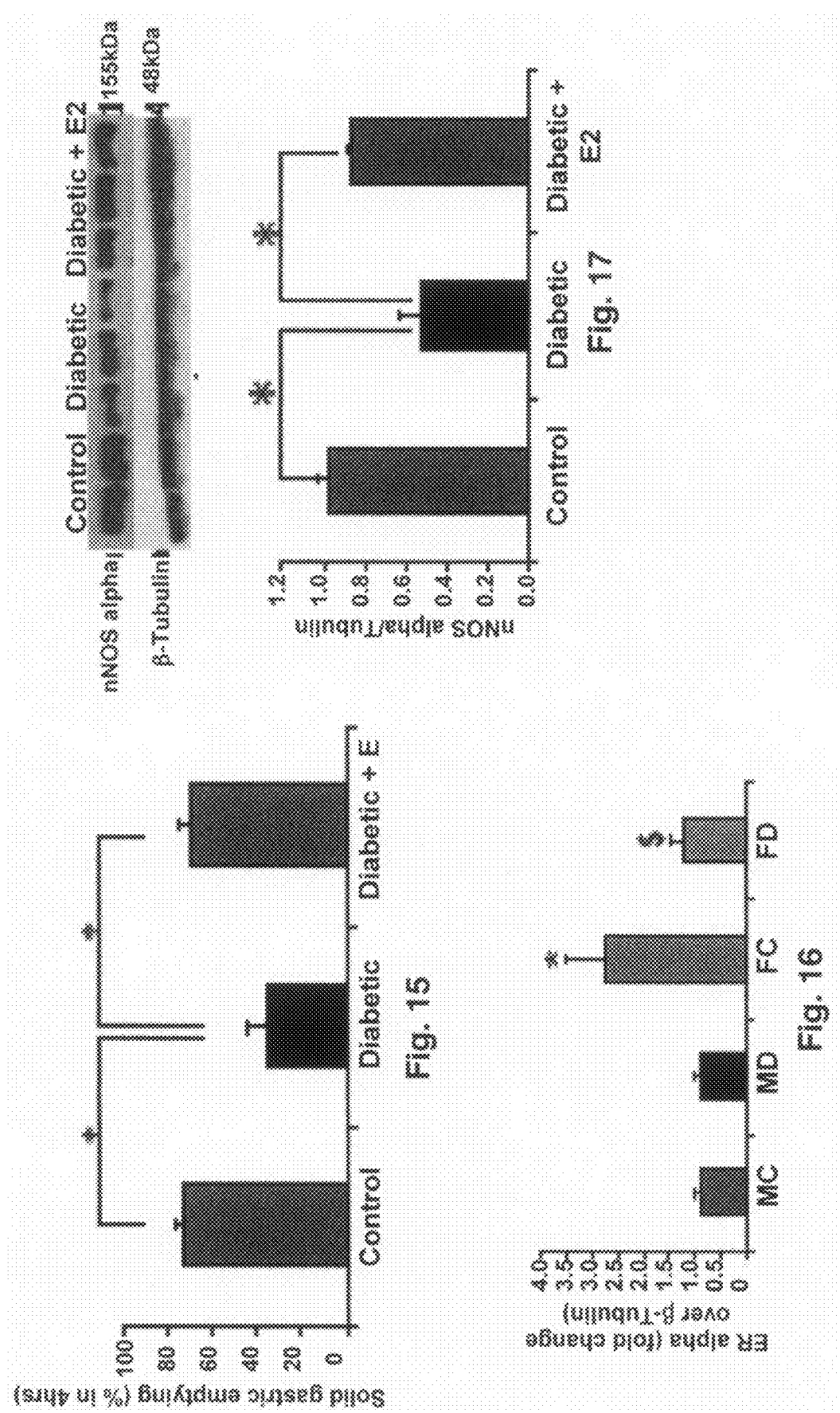

USES OF TETRAHYDROBIOPTERIN AND DERIVATIVES THEREOF

CROSS REFERENCE TO RELATED APPLICATION

This non-provisional application claims benefit of provisional application U.S. Ser. No. 60/855,275 filed on Oct. 30, 2006, now abandoned.

BACKGROUND OF THE INVENTION

1. Field of the Invention

The present invention relates to the fields of pharmacology and treatment of diseases, particularly gastrointestinal dysfunction. More specifically, the present invention discloses in one aspect the acceleration of gastric emptying by tetrahydrobiopterin (BH4) and derivatives thereof.

2. Description of the Related Art

Gastroparesis is a devastating disease affecting predominantly young women, with a female:male ratio of 4:1 (Soykan et al., 1998). Although a variety of diseases are associated with gastroparesis, the two most common subtypes are diabetes and idiopathic diabetic gastropathy (Camilleri., 2002; Bityutskiy et al., 1997), a syndrome of delayed gastric emptying leading to nausea, vomiting, postprandiol fullness, abdominal pain and early satiety. Because of its chronic and often intractable nature, the disorder has a tremendous impact on both patients and society (Bell et al., 2002; Revicki et al., 2004). Long standing and poorly-controlled diabetes results in the disturbance of several gastric functions such as gastric myoelectric activity, antroduodenal motor activity, gastric emptying and gastric visceral sensation (Parkman et al., 2004). Although delayed gastric emptying has long been taken as a hallmark of this condition, in recent reports most experts concur that this correlates poorly if at all with clinical symptoms (Rayner and Horowitz, 2005; Parkman et al., 2004). The biggest barrier to the development of effective therapy for gastroparesis has been the lack of understanding of its pathogenesis and/or pathophysiology. Consequently, treatment has been empirical and only partially effective, if at all, in relieving major symptoms.

Normally, gastric motility is regulated in large part by neurons of the enteric nervous system located in the muscle wall (Camilleri, 2002). These neurons are either excitatory (releasing acetylcholine) or inhibitory (releasing nitric oxide and vasoactive intestinal peptide). Nitric oxide (NO) is the principal non-adrenergic non-cholinergic (NANC) inhibitory neurotransmitter in the gastrointestinal tract and is produced by neuronal NOS, expressed in inhibitory enteric neurons (Coleski et al., 2005; Ishiguchi et al., 2000; Mizuta et al., 1999; Martinez-Cuesta, 1995; Takahashi, 2003; Nakamura, 1998; Nakao et al., 1998). NO activates soluble guanylate cyclase (sGC), producing an increase in the intracellular cyclic guanosine-3', 5'-monophosphate (cGMP), leading to muscle relaxation (Takahashi, 2003; Patil et al., 2005; Kim et al., 2003; Shah et al., 2000). Nitrergic signaling is particularly responsible for gastric accommodation and pyloric relaxation in response to a meal. The importance of NO in gastric function was established by the findings of pyloric hypertrophy and gastric dilation in mice with a targeted genomic deletion of neuronal nitric oxide synthase (nNOS−/−) (Huang et al., 1993; Mashimo et al., 2000). Vagal modulation of enteric neuronal function (both inhibitory and excitatory) also plays an important role in gastric physiology and is predominantly cholinergic in character (Undeland et al., 1997; Undeland et al., 1996; Li and Owyang, 2003).

Expression of nNOS is distinguished by a remarkable diversity. Different 5' mRNA variants of nNOS are reported in various tissues including the gut (Huber et al., 1998; Saur et al., 2000; Putzke et al., 2000; Saur et al., 2002; Panda et al., 2003). 5' mRNA variants of nNOS are generated either by alternative promoter usage resulting in different mRNA that encode for the same protein (nNOS alpha, 155 KDa) or alternative splicing encoding NH(2)-terminally truncated proteins (nNOS beta and gamma) that lack the PDZ/GLGF domain for protein-protein interaction (Saur et al., 2002; Panda et al., 2003; Saur et al., 2000; Kone et al., 2003). nNOS mutant mice, in which exon 2 (encoding for the PDZ/GLGF motif) and, consequently, full length nNOSalpha, was disrupted, maintain some nNOS expression due to presence of nNOS-beta and nNOSgamma. However, gastric function is severely affected with delayed gastric emptying (Huang et al., 1993; Mashimo et al., 2000). These studies suggest that nNOSalpha, but not other proteins, are essential for normal gastric motor function. The molecular mechanisms responsible for impaired NO function in diabetes remains incompletely understood with both a decrease (Watkins et al., 2000; Wrzos et al., 1997) and an increase (Adeghate et al., 2003) in nNOS expression being reported in the literature.

In diabetic gastric dysfunction, antral motility and the co-ordination of pressures between antrum and duodenum are diminished. Antral hypomotility has been recorded with intraluminal transducers in patients with diabetes mellitus. Abnormal gastrointestinal motility in diabetes mellitus is likely multifactorial in origin, reflecting disturbances in enteric and vagal neural activity as well as interstitial cells of Cajal (ICC) and smooth muscle function. Of these, enteric neuropathy may be particularly important (Martinez-Cuesta et al., 1995; Belai et al., 1985; Belai and Burnstock, 1987; Burnstock et al., 1988; Belai and Burnstock, 1990; Belai et al., 1991; Belai et al., 1988). Several studies of animal models of diabetes have convincingly shown disturbances in enteric nerves, particularly involving nitrergic nerves (Cellek., 2004; Cellek et al., 2005; Cellek et al., 2003; Buchan, 1990; Di Giulio et al., 1989). Impairment in nitrergic relaxation resulting from either neuronal loss or dysfunction may contribute to gastropathy in both streptozotocin (STZ) induced diabetes (Watkins et al., 2000; Jenkinson and Reid, 1995) as well as spontaneously diabetic male rats and mice (Takahashi et al., 1997). These disturbances provide a rational pathophysiological explanation for observations of decreased gastric compliance and pyloric relaxation noted in diabetic patients. In the absence of effective nitrergic output to muscle, gastric accommodation is impaired, resulting in early satiety and discomfort. Further, a functional obstruction at the gastric outlet due to a non-relaxing pylorus leads to delayed emptying (James et al., 2004; Cellek et al., 2003; Tougas et al., 1992; Ishiguchi et al., 2002). Diabetic rats and mice show defects in nitrergic relaxation and nNOS expression before neuronal degeneration in the pyloric sphincter and this was reversed by insulin treatment (Watkins et al., 2000; Cellek et al., 2003).

Several co-factors are known to be important for nNOS activity, including NADPH, calcium and tetrahydrobiopterin (BH4). Tetrahydrobiopterin regulates the homodimeric conformation of all three isoforms of NOS [endothelial(e)NOS; inducible(i)NOS; neuronal(n)NOS] (Cosentino and Luscher, 1999). BH4 also serves as a cofactor for three aromatic amino acid hydroxylases:phenylalanine (PAH), tyrosine hydroxylase (TH), and tryptophan hydroxylase (TPH). Additionally, BH4 is scavenger of oxygen-derived free radicals. BH4 has been clinically investigated as therapy for phenylketonuria (PKC), Parkinson's disease, dystonia, depression, Rett Syndrome, infantile autism, senile dementia, Alzheimer's disease and atherosclerosis. Lack of BH4 biosynthetic genes causes several abnormalities in mice. Incubation with saturating concentrations of tetrahydrobiopterin induces substantial conformational changes in the homodimeric structure of nNOS, yielding a stabilized nNOS dimer with maximal NO-producing activity (Gorren et al., 1996; Klatt et al., 1995). In mice, the highest levels of tetrahydrobiopterin are found in the liver, adrenals and stomach (Kobayahi et al., 1991). Tetrahydrobiopterin synthesis occurs via two distinct pathways: a de novo synthetic pathway which uses GTP as a precursor and a salvage pathway for preexisting dihydropterins (Thony et al., 2000; Gross and Levi, 1992) (FIG. 1).

GTP cyclohydrolase 1 (GTPCH1) is the rate-limiting enzyme for tetrahydrobiopterin de novo pathway leading to synthesis of dihydroneopterin triphosphate. Treatment of HEK293 cells with 2,4-diamino-6-hydroxypyrimidine (DAHP), an inhibitor of GTPCH1 leads to depletion of tetrahydrobiopterin, destabilization of the dimeric form of nNOS and enhanced ubiquitinylation of nNOS (Kamada et al., 2005). However, addition of sepiapterin, a precursor of tetrahydrobiopterin in the salvage pathway, completely reverses the effect of DAHP on nNOS destabilization (Kamada et al., 2005; Shang et al., 2005). In the absence of tetrahydrobiopterin, uncoupling of NO production occurs and electron flow from the reductase domain to the oxygen domain of nNOS is diverted to molecular oxygen rather than L-arginine. This leads to super oxide production; super oxide in turn not only degrades NO, but also forms peroxynitrite a potent oxidant that can rapidly oxidize BH4 to BH3+ and subsequently to BH2. BH2 may compete with tetrahydrobiopterin for nNOS binding, resulting in further impaired nNOS bioactivity.

There is considerable evidence supporting an important role for impairment in the tetrahydrobiopterin biosynthetic pathway in mediating dysfunction of NOS isoforms such as eNOS both in vivo and in vitro. DAHP, a GTPCH1 inhibitor reduces the sensitivity to acetylcholine (endothelium-dependent)-induced vascular relaxation (mediated by NO) in normal mice and this inhibitory effect was shown to be restored by addition of tetrahydrobiopterin in vitro (Pannirselvam et al., 2002). Treatment of diabetic vascular endothelial cells with sepiapterin (the tetrahydrobiopterin precursor in the salvage pathway, (FIG. 1), significantly improves NO synthesis. Preincubation of vascular rings with either tetrahydrobiopterin or sepiapterin enhances Ach(acetylcholine-)-induced relaxation in diabetic mice (Cosentino and Katusic, 1995; Mitchell et al., 2003; Pieper, 1997; Tsutsui et al., 1996). In addition, dietary supplementation of sepiapterin increases ACh-induced vascular relaxation in diabetic mice (Pannirselvam et al., 2003). In cultured endothelial cells exposed to high glucose (Cai et al., 2005), ex vivo gene transfer of GTPCH1 restores eNOS dimerization, attenuates impaired endothelium-dependent relaxation and increases NO production (Cai et al., 2005; Meininger et al., 2004). Selectively augmenting endogenous tetrahydrobiopterin levels by targeting over expression of GTPCH in endothelial cells in vivo preserves eNOS dimerization in streptozotocin (STZ)-induced diabetes mice (Cai et al., 2005; Alp et al., 2003). The beneficial effects of tetrahydrobiopterin supplementation in reversing impaired endothelium dependent relaxation have also been demonstrated in human patients. BH4 therapy was shown to be useful in improving endothelium-dependent relaxation in patients with hypercholesteromia (Stroes et al., 1997), venous conduits used for coronary artery bypass graft surgery (Maier et al., 2000), patients with type II diabetes (Heitzer et al., 2000), normal epicardial arteries (Setoguchi et al., 2001) and smokers (Heitzer et al., 2000).

Furthermore, there is increasing evidence of gender-related differences in gastric emptying. The effect of gender in a healthy population on gastric emptying remains controversial though it appears that women may have slower solid and liquid emptying. Ambulatory antroduodenal manometry has shown shorter migrating motor complex (MMC) periods in women compared to men (Aytug et al., 2001). The mechanisms responsible for these differences are not completely understood. In a recent study of duodenojejunal motility, women in the follicular phase were found to exhibit motor activity similar to that of men (Soffer et al., 1998). On the other hand, another study demonstrated attenuated postprandial antral contractile activity in the follicular phase of women compared to men (Knight et al., 1997). Additionally, animal studies demonstrated that the gastric emptying rate was slower in ovary-intact female rats compared to ovariectomized (depletion of ovarian hormones; estrogen and progesterone) female rats (Chen et al., 1995; Coskun et al., 1995). Furthermore, studies suggested that estradiol-17β (E2) but not progesterone (P4) may be responsible for delayed gastric emptying and increased nitrergic system. In addition to this, studies suggest that P4 treatment decreased the resting tension fundus, inhibited mean contractile amplitude of antrum and the motility index of pylorus in rats (Wang et al., 2003). Diabetes induction decreases both the circulatory E2 and P4 levels in both women and female rats (Resnick and Howard, 2002; Mankhey et al., 2005; Leonelli et al., 2007; Veiga et al., 2006; Caruso et al., 2007).

Sex steroid hormones mediate their biological actions through their respective nuclear (genomic) cytoplasmic/membrane (non-genomic, rapid via nitric oxide elevation) receptors (Boonyaratanakornkit and Edwards, 2007). Estrogen receptors (ERs) and progesterone receptors (PRs) are expressed as two proteins: ERα and ERβ, and PR-A and PR-B. ERα and ERβ are expressed from two different genes, whereas PR isoforms are produced from alternate use of two promoters from the same gene. Sex steroid hormone receptors require both a ligand (sex hormones, insulin, growth factors etc) and interactions with other proteins, such as coregulators, to achieve maximal transcriptional activation of genes. Female sex steroids (both $E_2$ and $P_4$) has multiple beneficial actions that includes neuroprotection, maintaining glucose homeostasis in both health and diabetes (Leonelli et al., 2007; Caruso et al., 2007; Boonyaratanakornkit and Edwards, 2007; Barros et al., 2006). In particular, estrogen has both genomic and rapid nongenomic effects via its receptors on vascular endothelium, including activation of NO synthesis (Widder et al., 2003; Cid et al., 2002). Previous studies demonstrated that nNOS is involved in estrogen mediated neuroprotection in neuroblastoma cells (Wen et al., 2004; Murphy and Steenbergen, 2007; Scordalakes et al., 2002; Garcia-Duran et al, 1999; Gingerich and Krukott, 2005; El-Sakka et al., 1999). The role of progesterone and its metabolites via PR's on NO mediated cardioprotection has been recently reported in postmenopausal women (Simoncini et al., 2007). Upon binding to their respective receptors, sex steroids, utilizes several cell signaling mechanisms such as cyclic adenosine monophosphate (cAMP), cyclic guanosine monophosphate (cGMP), mitogen-activated protein kinases (MAPKs), phosphatidylinositol 3-kinase (PI3K)/Akt pathways, for their actions. In the genomic pathway, sex steroids binds to their cytosolic/nuclear receptors, leading to activation of MAPK/Akt, increase gene transcription and upregulate nitric oxide production. In non-genomic pathway, sex steroids binds to their membrane receptors, which are coupled to increased $Ca^{2+}$ release from the endoplasmic reticulum, and stimulate MAPK/Akt/PI3K pathway, leading to NO production. NO diffuses into the smooth muscle cells, binds to adenylate cyclase (AC) or guanylate cyclase (GC) and increases cAMP or cGMP respectively. Significant actions for sex steroids have been noticed in the gastrointestinal tract in various experimental animal models and human clinical settings (Kawano et al., 2004). Shah et al studies demonstrated that estrogen treatment increases nNOS positive neurons in the female rat stomach. Several studies demonstrated that both ERs are primarily localized in nerve cells of the gut (Shah et al., 2001; Kawano et al., 2004; Campbell-Thompson et al., 2001).

Estrogen treatment elevates both the expression of GTPCH1 and BH4 levels in rat brain neurons through estrogen receptors (Serova et al., 2006; Serova et al., 2004; Lam et al., 2006). In vitro hyperglycemia decreases both BH4 biosynthesis and nitric oxide and estrogen supplementation restored this effect via ERα in bovine aortic endothelial cell culture (Miyazaki-Akita et al., 2007). Diabetes induction decreases the circulatory estrogen and progesterone levels in both women and female rats. Previous reports demonstrated that estrogen receptors are localized in stomach enteric neurons. The beneficial role for $E_2$ treatment on both GTP cyclohydrolase1 (GTPCH1) expression and nNOS expression has been well demonstrated.

Despite this, the prior art is deficient in the role played by tetrahydrobiopterin or derivatives thereof in the nitric oxide induced diabetic gastroparesis. Additionally, the prior art is also deficient in understanding the gender-related differences in gastric emptying. The present invention fulfills this longstanding need and desire in the art.

SUMMARY OF THE INVENTION

In one embodiment of the present invention, there is provided a method of restoring gut motility in an individual. This method comprises administering a pharmacologically effective amount of sepiapterin, tetrahydrobiopterin, sex steroid hormone or a derivative thereof or a compound(s) that increases the expression and/or activity of enzymes molecules that are critical in the synthesis of tetrahydrobiopterin or compounds that stimulate steroid receptor to the individual, thereby restoring gut motility in the individual.

In another embodiment of the present invention, there is a method of determining the risk of developing gastrointestinal dysfunction in an individual. Such a method comprises obtaining a biological sample from the individual, determining the level of tetrahydrobiopterin, activity level of enzymes or molecules that are critical in the synthesis of tetrahydrobiopterin, activity level of sex steroid hormones, sex steroid hormone receptor level or a combination thereof in the individual. The level of tetrahydrobiopterin activity level of the enzymes or the molecules, the level of sex steroid hormone activity, the sex steroid hormone receptor level or a combination thereof in this sample are then compared with the level of tetrahydrobiopterin activity level of the enzymes or the molecules, the level of sex steroid hormone activity, the sex steroid hormone receptor level or a combination thereof in the sample of control individual, where a reduced level of tetrahydrobiopterin, activity level of the enzymes or the molecules, the level of sex steroid hormone activity, the sex steroid hormone receptor level or a combination thereof compared to the level in the sample of control individual indicates that the individual has more risk of developing gastrointestinal dysfunction.

In yet another embodiment of the present invention, there is a method of determining risk of developing gastrointestinal dysfunction in an individual. This method comprises detecting variations in one or more genes encoding one or more enzymes that are critical in the synthesis of tetrahydrobiopterin, encoding one or more receptors of sex steroid hormones, mutations in BH4 biosynthesis genes or mutations in one or more genes encoding hormones associated with diabetes or a combination thereof in a sample of the individual, where presence of at least one of variations or mutations in one or more genes in the sample of the individual compared to one or more genes in the control sample indicates that the individual is at risk of developing gastrointestinal dysfunction.

BRIEF DESCRIPTION OF THE DRAWINGS

FIG. 2A shows gender and diabetes induced changes in solid gastric emptying in rats. The rate of gastric emptying was measured during the 4 hours experimental time. FIG. 2B shows that dietary supplementation (25 mg/kg b.w./day/rat), completely restored gastric emptying in female rats. *$p<0.05$. ANOVA.

FIGS. 3A-3B show that chronic diabetes impaired intragastric antrum pressure and sensitivity to L-NAME in female rats. The intragastric antrum pressure (IGAP) was measured in normal and diabetic male (FIG. 3A) and female (FIG. 3B) rats. The transducer pressure catheter was introduced into the gastric antrum cavity 5 mm proximal to the pylorus to record IGAP (mmHg×sec). After recording the baseline IGAP, $N^G$-nitro-L-arginine methyl ester (L-NAME, 200 mg/day/kg body weight (BW)/rat) was administered subcutaneously in the same rats by osmotic mini-pumps (Alza, Palo Alto, Calif., model 2mL1 with a pumping rate of 10 μl/hour) for 4 days. All subsequent studies were performed 1 week after surgery in overnight fasted rats that were awake and in a free-moving state. Pressure recordings were performed at least 2-3 hours between 9-12 am. Bilateral ovariectomy was performed as reported previously. Dietary BH4 (25 mg/day/kg body weight (BE)/rat). *$p<0.05$. ANOVA.

FIGS. 4A-4C show that chronic diabetes impairs nitrergic (NO produce neurons) relaxation but does not result in a loss of nitrergic neurons in female gastric tissues. FIG. 4A shows effect of diabetes on gastric nitrergic relaxation in response to transmural nerve stimulation (2 Hz) in age-matched male and female rats. Active tone was induced initially with 30 μM 5-hydroxytryptamine. The nitric oxide (NO) dependence relaxation in female control (FC) and female diabetic (FD) groups was confirmed by preincubation with the NO inhibitor, L-NAME (LNM, $10^{-4}$ M). Each point represents mean ±SEM from 4-6 animals in each group. *significant inhibition with L-NAME, #*significant inhibition with L-NAME, $p<0.05 for FD vs FC. ANOVA. AUC. FIG. 4B shows effect of nitric oxide donor, DETA-NONOate on gastric relaxation. Gastric pyloric tissue segments from normal and diabetic female rats were preincubated with DETA-NONOate for 10-15 minutes and changes in relaxation were analysed. FIG. 4C shows tunnel staining (counterstaining with hematoxylin) in female rat gastric pylorus myenteric neurons. No staining for TUNNEL was noticed in diabetic gastric tissues compared to controls indicating that there were no neuronal cell death. Arrows indicate a portion of myenteric plexus region. Magnifications are 200×.

FIGS. 5A-5D show that chronic diabetes reduces nNOS-alpha protein expression in female gastric tissues. nNOS mRNA (FIG. 5A), nNOS total protein (alpha, beta and gamma, FIG. 5B) and nNOS alpha protein expression in female control (FC) and female diabetes (FD) were compared. Densitometric analysis followed by a ratio of nNOS mRNA to 18 S (FIG. 5A) or nNOS protein to β-tubulin (FIG. 5B) were calculated. The bars represent mean ±SEM. *p<0.05 FC vs FD. FIG. 5D show nNOS dimer (310 KDa, top band) and monomer (155 KDa, bottom band) ration in gastric tissue of female control (FC) and female diabetes (FD). Densitometric analysis followed by ration of nNOS alpha dimerization to beta-tubulin were calculated. The bars represent mean ±SEM, n=3-4, *p<0.05 control vs diabetic, ANOVA.

FIG. 6 shows that chronic diabetes reduces NO release in female gastric LM-MP tissues. NO release was measured by readily available kit in female control (FC) and female diabetic (FD) gastric LM-MP tissues. Mean ±SEM, (n=3) *p<0.05.

FIG. 7 shows that chronic diabetes reduced BH4 content in gastric pylorus tissues. BH4 levels were measured by HPLC in female control (FC) and female diabetic (FD) gastric pylorus tissues. mean ±SEM, (n=3), *p<0.05.

FIG. 8 shows effect of endogenous BH4 inhibition by DAHP (10 mM, 3 hour incubation) on nitrergic function (n=2). Basal tone relaxation studies in gastric tissues were performed after EFS stimulation at 2 and 10 Hz (n=2). In vitro treatment with DAHP, reduced nitrergic relaxation after EFS stimulation. AUC=area under curve.

FIGS. 9A-9B shows in vitro effects of DAHP, an inhibitor for GTPCHI (first and rate limiting enzyme in BH4 biosynthesis) on nNOS dimerization and NO release in healthy female rat gastric LM-MPs. Gastric LM-MPs were incubated for 48 hrs in the presence or the absence of DAHP (10 mM) and nNOS dimerization (FIG. 9A) in tissues and NO release (FIG. 9B) in the media were assessed. (n=3).

FIG. 10 shows effect of chronic diabetes on GTPCH1 protein expression in rat female stomachs (n=3), *p<0.05.

FIG. 11 shows effect of chronic diabetes on GTPCH1 mRNA levels in female patients. GTPCH1 protein expression was reduced in female diabetic patient gastric biopsies. Full thickness gastric biopsies were used for Affymetric gene arrays (n=2).

FIG. 12A-12C show that supplementation of dietary BH4 improves solid gastric emptying, nNOS activity and nitrergic relaxation in female diabetic gastric fundal tissues. FIG. 12A shows effect of exogenous BH4 (100 μM, 30 minutes) on nitrergic relaxation in female control (FC) and diabetic (FD) rats. Basal tone relaxation studies in gastric tissues were performed after EFS stimulation (n=2). Exogenous BH4 increased nitrergic relaxation in female diabetic gastric fundal tissues. AUC=area under curve. FIG. 12B shows that chronic diabetes delayed gastric emptying for solids in female rats. In vivo dietary BH4 supplementation (25 mg/Kg body weight/day/rat/3 Wk), completely restored delayed gastric emptying in female rats. (n=4-6). *p<0.05. FIG. 12C shows effect of dietary BH4 on gastric nNOS activity in female diabetic rats. Diabetic induction reduced nNOS activity in gastric tissues. Dietary BH4 supplementation partially restored altered gastric emptying in female diabetics (n=2).

FIGS. 13A-13B show that supplementation with dietary BH4 improves intragastric pressure, nNOSalpha protein expression in female diabetic gastric tissues. FIG. 13A shows effect of dietary BH4 on intragastric pressure (IGP, mmHg× sec) and FIG. 13B shows gastric nNOS alpha protein expression in female diabetic rats. Diabetic induction elevated IGP and reduced nNOSalpha expression in gastric tissues. Dietary BH4 supplementation completely restored altered IGP and nNOS alpha protein expression (n=4).

FIG. 14 shows that estradiol-17beta delays gastric emptying for solids in healthy females. The OVX female animals were implanted subcutaneously (per kg body weight) with 21 day release of either Estradiol-17beta (E2; 2 mg), P4 (20 mg) or placebo (control) pellets. Solid gastric emptying was then assessed. Data were mean ±SEM, n=3-4. *p<0.05 compared to control group.

FIG. 15 shows that chronic diabetes delayed gastric emptying in female rats. Estradiol-17 beta (E2, 2 mg/kg b.w/21 days) treatment reversed delayed gastric emptying in diabetic females. Data were mean ±SEM, n=3-4. *p<0.05.

FIG. 16 shows effect of chronic diabetes on estrogen receptor alpha (ER-alpha) mRNA in male and female rat stomachs. MC, male control; FC, female control; MD, male diabetic; FD, female diabetic. n=3-4, *p<0.05 compared to MC, $p<0.05 compared to FC.

FIG. 17 shows that Estradiol-17beta restores reduced nNOSalpha protein expression in diabetic female rat gastric tissues. The diabetic female animals were implanted subcutaneously (per kg b.w) with 21 day release of E2 (2 mg) or placebo (control) pellets. nNOSalpha protein expression was then measured. Data were mean ±SEM, n=3. *p<0.05 compared to control group.

DETAILED DESCRIPTION OF THE INVENTION

Figure 1:
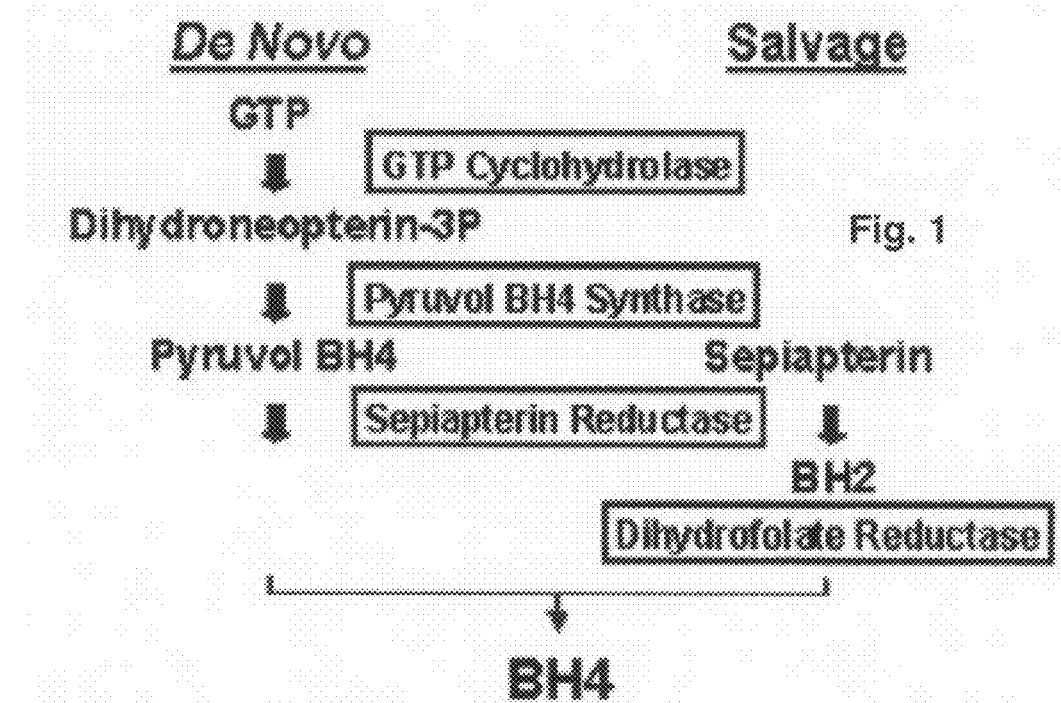
FIG. 1 shows biosynthesis of tetrahydrobiopterin (BH4). BH2=dihydrobiopterin, GTP=guanosinetriphosphate.

Abnormalities in gastric motility occur in 20-55% and up to 30% of patients with Type I (insulin-dependent) and Type II diabetes (non-insulin-dependent), respectively. Symptoms of diabetic gastropathy ranges from mild dyspepsia to recurrent vomiting and abdominal pain. Despite the high frequency of occurrence of diabetic gastric dysfunction, its pathogenesis remains poorly understood. Additionally although up to 80% of the patients with diabetic gastroparesis are women, the mechanisms responsible for these gender differences remain completely unknown.

Nitric oxide (NO), synthesized by neuronal nitric oxide synthase (nNOS) in the myenteric neurons is a major regulator of gastrointestinal motility in health. Several lines of experimental work also indicate a potentially important role for nitrergic dysfunction in the pathogenesis of diabetic gastroparesis. The present invention investigated whether gender differences in nitrergic control of gastric motility accounted for observed vulnerability of females to diabetic gastroparesis. Briefly, diabetes was induced by streptozotocin (STZ; 55 mg per kg body weight, i.p.) and experiments were conducted 12 weeks after diabetes induction. The nNOS protein expression and dimerization were examined using COOH— and NH2-terminal antibodies, respectively. The COOH-terminal antibody detects all forms of nNOS whereas the NH2-terminal antibody detects only wild type (full length) nNOS alpha proteins. Under normal conditions, both dimers and monomers of nNOS protein were intensified at 155 KDa. However, low temperature (LT) SDS-PAGE separate NOS dimers (310 KDa) and monomers (155 KDa) from non-boiled sample homogenates.

In summary, the present invention discloses that significant gender differences in gastric nitrergic function exists in both healthy and diseased individuals. These differences are not accounted for by changes in the neuronal loss or nNOS expression but correlate with changes in nNOS dimerization. Females with diabetes show a selective reduction in nitrergic relaxation of the pylorus, accompanied by impairment in nNOS dimerization, nNOS activity, NO release and decreased tetrahydrobiopterin and GTPCH1 levels. Additionally, diabetes induction decreases estrogen receptor (ER) alpha expression in female gastric tissues. Further, in vivo experiments demonstrate that dietary BH4 delayed gastric emptying, intragastric pressure (IGP) and nNOS activity in female diabetics. Additionally, it was observed that diabetic females exhibited decreased body weights. Pup weights have been reported to have drastically reduced in PTPS ($2^{nd}$ enzyme in de novo BH4 synthesis pathway) knockout mice. Studies have also demonstrated that IGF1 levels are reduced up to 7 fold in BH4 deficient patients. In the present invention, it was observed that BH4 supplementation restored the body weights in female diabetic rats. Taken together, this suggests that BH4 may have a beneficial role in improving total body weights and survival perhaps by involving IGF1.

Furthermore, in vitro experiments suggest that endogenous tetrahydrobiopterin inhibition reduced gastric nNOS dimerization, NO release and nitrergic relaxation. Therefore, BH4 supplementation may restore nitrergic relaxation in diabetic gastric tissue. Reactive Oxygen species (ROS) staining was higher in female diabetic gastric cross sections. BH4 treatment reduced the intensity of staining in diabetic females. These data demonstrated that BH4 acts as antioxidant as well as anti-inflammatory agent in other disease states. Additionally, serum sex hormones and the expression of gastric ER-alpha was decreased after diabetic induction in female rats. In vivo estradiol-17beta ($E_2$) treatment delayed solid gastric emptying in healthy females due to elevated levels of nNOS alpha. Conversely, $E_2$ treatment normalized delayed gastric emptying and decreased nNOSalpha protein expression in female diabetic rats. Additionally, tetrahydrobiopterin decreased elevated TNF-alpha levels in female diabetic rat circulation. Elevated TNF alpha might have harmful effects such as increasing oxidative stress factors and apoptosis (including neuropathy) in multiple tissues, altering nitric oxide levels and causing gastroparesis in diabetic patients.

Thus, the present invention discloses a method of regulating levels of agonists and antagonists of gut motility by contacting a cell in gastric tissue with a pharmacologically effective amount of sepiapterin, tetrahydrobiopterin, sex steroid hormone or a derivative thereof or a compound(s) that increases the expression and/or activity of enzymes or molecules that are critical in the synthesis of tetrahydrobiopterin to the individual, thereby regulating the levels of agonists and antagonists of gut motility. Examples of the agonists of gut motility may include but are not limited to neuronal nitric oxide synthase or monoamine neurotransmitters and those of antagonists of gut motility may include but are not limited to free radicals, NF-κB or inflammatory cytokines.

Overall, the findings discussed herein indicate that diabetes negatively affects both female sex steroid hormones and gastric tetrahydrobiopterin biosynthesis. This results in decreased nNOS activity and NO production, thereby impairing nitrergic relaxation. Thus, supplementation of the diet of individuals diagnosed with, suspected of or likely to suffer from with tetrahydrobiopterin or derivatives thereof or with compound(s) that increase the expression and/or activity of enzymes or molecules that are critical in the synthesis of tetrahydrobiopterin and/or sex steroid hormones or derivatives thereof might restore impaired nNOS activity and function. The present invention contemplates that use of sepiapterin, tetrahydrobiopterin or derivatives thereof and sex steroid hormones or derivatives thereof is significant since the methods discussed herein can be used to treat gastroparesis. Specifically, the gastroparesis may be caused due to diabetes, adrenal or thyroid gland dysfunctions, scars or fibrous tissue from ulcers or tumors, drugs that weaken the stomach, previous stomach surgery, anorexia, bulimia, neurologic or brain disorders, lupus erythematosus or scleroderma.

Furthermore, the administration of sepiapterin, tetrahydrobiopterin, sex steroid hormones or a derivative thereof or compound(s) that increase the expression and/or activity of enzymes or molecules that are critical in the synthesis of tetrahydrobiopterin is also be useful in restoring in restoring gut motility in individuals with esophagus and/or small or large intestinal bowel disorders caused by impaired nitric oxide synthase and/or monoamine neurotransmitter function and/or gut related diseases. Examples of such gut related disease include but are not limited to pancreatitis, colon cancer, colonic inflammation, Crohn's disease, inflammatory bowel disease or irritable bowel syndrome. Furthermore, the levels of BH4 and/or levels of enzymes such as GTP cyclohydrolase 1 or other molecules critical in BH4 synthesis may be used as a diagnostic marker to predict the risk of developing gastroparesis. Additionally, it is also contemplated that the variations in the genes encoding BH4, the enzymes (GTP cyclohydrolase 1) or other molecules critical in BH4 synthesis may be helpful in predicting predisposition to developing gastroparesis. Hence, this could be a clinically useful diagnostic test.

The present invention is directed to a method of restoring gut motility in an individual, comprising administering a pharmacologically effective amount of sepiapterin, tetrahydrobiopterin, sex steroid hormone or a derivative thereof or a compound(s) that increases the expression and/or activity of enzymes, molecules that are critical in the synthesis of tetrahydrobiopterin or compounds that stimulate steroid receptor to the individual, thereby restoring gut motility in the individual. This method may further treat or prevent a gut-related disorder in the individual. The causes of the prevention or treatment of the disorder are not limited to but may include restoration of intragastric pressure, restoration of body weight, improvement in gastric emptying, in symptoms of gastroparesis, in mast cell diversity and function, in blood flow, prevention of free radical induced-damage or free radical-induced apoptosis of neurons or other cellular components or a combination thereof in the individual. The gut-related disorder may include but is not limited to gastroparesis, esophagus and/or small and large intestinal bowel disorders caused by impaired nitric oxide synthase and/or monoamine neurotransmitter function, pancreatitis, colon cancer, colonic inflammation, Crohn's disease, inflammatory bowel disease or irritable bowel syndrome. The cause of gastroparesis in such individuals may include but is not limited to diabetes, adrenal or thyroid gland dysfunction, scars or fibrous tissue, drugs that weaken the stomach, previous stomach surgery, anorexia, bulimia, neurologic or brain disorders, lupus erythematosus or scleroderma. Additionally, examples of the drugs that weaken the stomach may include but are not limited to tricyclic antidepressants, calcium blockers or drugs used to treat irritable bowel syndrome.

The administration of compounds discussed supra may restore body weight, restore dimerization of the neuronal nitric oxide synthase, restore activity of the neuronal nitric oxide synthase, restore functions of monoamine neurotransmitters, lower the level of free radicals, suppress stimulation of NF-κB, suppresses inflammatory signaling, lower the level (s) of inflammatory cytokine(s) or a combination thereof. Examples of the monoamine neurotransmitters may include but are not limited to dopamine, epinephrine, norepinephrine, serotonin or melatonin and that of the inflammatory cytokine may include but is not limited to TNF-alpha.

Additionally, the sepiapterin, the tetrahydrobiopterin or the derivative thereof or a compound(s) that increases the expression and activity of enzyme(s) or molecule(s) that are critical in the synthesis of tetrahydrobiopterin may be administered either alone or in combination with other medications. Example of the enzyme inhibited may include but is not limited to GTP cyclohydrolase 1. Further, example of the derivative of sepiapterin may include but is not limited to 7,8-dihydrobiopterin, the derivative of tetrahydrobiopterin may include but is not limited to 6R-tetrahydrobiopterin, lipoic acid, dihydrolipoic acid, a salt thereof or a combination thereof and the sex steroid hormone may include but is not limited to estradiol-17beta, phytoestrogens, isoflavones or progesterone. The compounds that stimulate sex steroid hormone receptors such as estrogen receptor or progesterone receptor may include but is not limited to agonists for steroid hormone receptors, growth hormones or insulin.

The present invention is also directed to a method of determining the risk of developing gastrointestinal dysfunction in an individual, comprising obtaining a biological sample from the individual, determining the level of tetrahydrobiopterin, activity level of enzymes or molecules critical in the synthesis of tetrahydrobiopterin, activity level of sex steroid hormones, sex steroid hormone receptor level or a combination thereof; and comparing the level of tetrahydrobiopterin, activity level of the enzymes or the molecules, activity level of sex steroid hormones, sex steroid hormone receptor level or a combination thereof in the sample of the individual with the level of tetrahydrobiopterin activity, level of the enzymes or the molecules, activity level of sex steroid hormones, sex steroid hormone receptor level or a combination thereof in the sample of a control individual where a reduced level of tetrahydrobiopterin, activity level of the enzyme or the molecules, activity level of sex steroid hormones, sex steroid hormone receptor level or a combination thereof compared to the level in the sample of the control individual indicates that the individual has more risk of developing gastrointestinal dysfunction. Generally, the individual who may benefit from such a method may include but is not limited to one with impaired nitric oxide synthase and/or monoamine neurotransmitter function, diabetes, elevated levels of NF-κB and/or inflammatory cytokines, adrenal or thyroid gland dysfunctions, scars or fibrous tissue, previous stomach surgery, anorexia, bulimia, neurologic or brain disorders, lupus erythematosus, scleroderma, or who is taking drugs that weaken the stomach. Examples of the gastrointestinal dysfunction may include but is not limited to gastroparesis, inflammatory bowel disease, esophagus or small and large intestinal bowel disorders, pancreatitis, colon cancer, colonic inflammation, Crohn's disease or irritable bowel syndrome. Example of the biological sample may include, but is not limited, to serum, gut, vasculature or reproductive organs. All other aspects regarding the example of inflammatory cytokine, drugs that weaken the stomach, and the enzyme whose activity or level is determined is the same as discussed supra.

The present invention is also directed to a method of determining risk of developing gastrointestinal dysfunction in an individual, comprising: detecting variations in one or more genes encoding one or more enzymes that are critical in the synthesis of tetrahydrobiopterin, encoding one or more receptors of sex steroid hormones, mutations in BH4 biosynthesis genes or mutations in one or more genes encoding hormones associated with diabetes or a combination thereof in a sample of the individual, where presence of at least one of variations or mutations in one or more genes in the sample of the individual compared to one or more genes in the control sample indicates that the individual is at risk of developing gastrointestinal dysfunction. All other aspects regarding the individual benefiting from such a method, the type of inflammatory cytokine, the examples of drugs that weaken the stomach, the examples of gastrointestinal dysfunction, the example of enzyme whose gene variation is assessed and the examples of samples used to determine the variations is same as discussed supra. The genes encoding hormones associated with diabetes are known in the art. These include but are not limited to insulin or glucagon.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. As used herein, the term "contacting" refers to any suitable method of bringing the composition described herein into contact with a cell of gastric tissue. In vitro or ex vivo this is achieved by exposing the cell to the composition in a suitable medium. For in vivo applications, any known method of administration is suitable as described herein. As used herein, the term "compound" or "agonist" or "antagonist" means a molecular entity of natural, semi-synthetic or synthetic origin that either activates or blocks, stops, inhibits, and/or suppresses biosynthetic pathway of tetrahydrobiopterin. An agonist will activate the pathway while the antagonist will block, inhibit, and/or suppress the pathway As used herein, "sepiapterin, tetrahydrobiopterin or derivative thereof" may be of a natural, semi-synthetic or synthetic origin that restore dimerization of neuronal nitric oxide synthase and activity of neuronal nitric oxide synthase, lower TNF alpha level, NF-kB, free radicals, restore nitric oxide level and restore nitrergic relaxation of gut tissue. These compounds may be administered independently, either systemically or locally, by any method standard in the art. Dosage formulations of these compounds may comprise conventional non-toxic, physiologically or pharmaceutically acceptable carriers or vehicles suitable for the method of administration and are well known to an individual having ordinary skill in this art.

The compounds described herein may be administered independently or in combination with another drug or compound that is routinely used to treat other symptoms of that specific disorder and may comprise one or more administrations to achieve, maintain or improve upon a therapeutic effect. It is well within the skill of an artisan to determine dosage or whether a suitable dosage of the composition comprises a single administered dose or multiple administered doses. An appropriate dosage depends on the subject's health, the restoration of mucosal barrier function or attenuation of inflammation, the route of administration and the formulation used. Examples of such drugs may include but are not limited to tricyclic antidepressants, calcium blockers or drugs used to treat irritable bowel syndrome.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Chronic Diabetes Delayed Solid Gastric Emptying in Rats

Figure 2A:
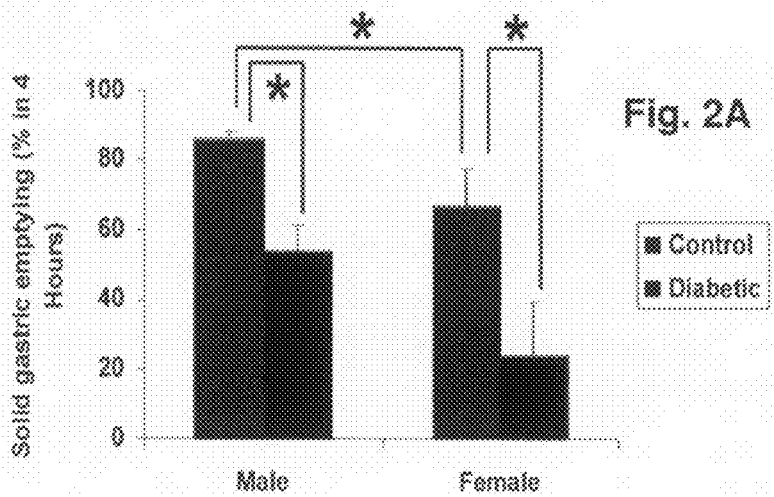
FIGS. 2A-2B show that chronic diabetes delayed solid gastric emptying in female rats.
Figure 2B:
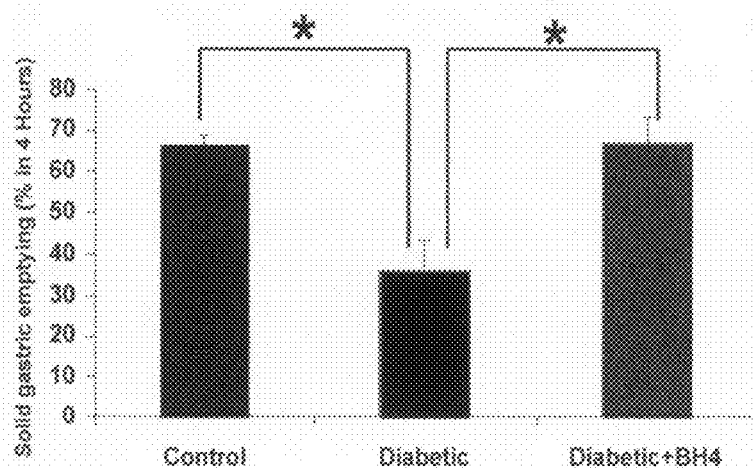

The present invention investigated whether solid gastric emptying (GE) is slower in male and female rats after diabetes induction. Additionally, whether dietary tetrahydrobiopterin attenuated the delayed gastric emptying in female diabetic rats was also examined. Diabetes induction significantly delayed gastric emptying in both male and female rats (FIG. 2A). However, females showed severe gastroparesis compared to males after diabetes induction. Interestingly, tetrahydrobiopterin supplementation completely restored gastric emptying in female diabetic rats (FIG. 2B).

EXAMPLE 2

Chronic Diabetes Impairs Intragastric Antrum Pressure and Sensitivity to L-NAME in Female Rats Intragastric pressure (IGP) was measured using ambulatory telemetric device. The technique used herein is similar to that of the ambulatory manometric method used in humans to measure contractions of gastric antrum. A previous study had reported a decrease in antral contractility in women compared to age matched men by using dynamic antral scintigraphy and antriduodenal manometry. The intragastric pressure was observed herein to be lower in female compared to male rats (FIGS. 3A, 3B). L-NAME treatment significantly elevated IGAP in females and this was decreased in male rats. No change in intragastric pressure was noticed with L-NAME treatment in female rats. However, males showed an increase in intragastric pressure after L-NAME treatment (FIGS. 3A, 3B). Additionally, dietary tetrahydrobiopterin completely restored the elevated intragastric pressure in female diabetic rats. These observations suggested that female are more dependent on both ovarian estrogens and nitric oxide system in gastric motility functions compared to male rats. This also suggested that tetrahydrobiopterin supplementation may play a critical role in regulating nNOS activity and dimerization in female gastric tissues. The present invention contemplates investigating time dependent changes in intragastric pressure in the onset of diabetes and whether supplementation with BH4 and sex hormones restored impaired intragastric pressure in diabetic females.

EXAMPLE 3

Chronic Diabetes Impairs Nitrergic (Neurons Produce NO) Relaxation in Female Gastric Tissues The nitrergic relaxation was investigated after electrical field stimulation (EFS). Gastric antrum (FIG. 4A) strips obtained from female diabetic (FD) rats showed an increase in nitrergic relaxation compared to female control (FC) group. In addition, it was also observed that preincubation with tetrodotoxin (TTX, 30 minutes, 1 μM) abolished nitrergic relaxation (data not shown). Further, the NO donor, (z)-1-[2-(2-amino ethyl)-N-(2-ammonioethyl)amino]diazen-1-ium-1,2-diolate (DETA-NONOate, 100 μM) was used to test whether the smooth muscle response to nitrergic signaling remained intact in diabetes. The data presented herein indicates that the relaxation responses to DETA-NONOate were similar in both control and diabetic gastric tissues obtained from female rats (FIG. 4B).

Thus, it appeared that females relied on nitrergic control of gastric motility to a greater extent than males and hence, were more vulnerable to alterations of this system induced by diabetes. The present invention contemplates examining the effects of diabetes, supplementation of BH4 and female sex hormones on nitrergic relaxation in female gastric fundus, antrum and pyloric LM-MP tissues.

Longitudinal muscle-myenteric preparations from the stomach were utilized to examine whether nNOS containing neurons were affected by diabetes in male and female rats. Diabetes did not alter nNOS positive neurons in gastric LM-MPs compared to the control group. In addition, TUNEL staining demonstrated that chronic diabetes did not induce significant apoptosis (n=3) in either female or male diabetic gastric pyloric myenteric neurons (FIG. 4C) compared to control groups. These data suggested that the loss in nitrergic relaxation in diabetes (FIG. 4A) was not due to neuronal degeneration.

EXAMPLE 4

Chronic Diabetes does not Alter nNOS Expression in Female Gastric Tissues

Real-time RT-PCR and Western blotting studies were performed in control and diabetic female rats. It was observed that diabetes resulted in a further increase in nNOS total (COOH-terminal antibody) protein (alpha, beta and gamma) expression in female gastric tissues (FIGS. 5A and 5B). Additionally, the expression of nNOS was significantly higher ($p<0.05$) in female control gastric pylorus compared to male control group. However, nNOSα protein is (NH2 terminal antibody) decreased in female diabetic gastric tissues compared to control group. These data suggested that changes in nNOSα but not total nNOS (alpha, beta and gamma) expression was critical for impaired nitrergic relaxation in diabetic gastric tissues (FIG. 4A). Based on this, it is suggested that increases observed in total nNOS protein could be due to increases in nNOS β and nNOS gamma which are not important for gastric motility functions as reported previously using nNOS knock-out mice. Hence, the present invention contemplates examining the time dependent changes in total nNOS and nNOS alpha protein expression in female gastric fundus, antrum and pyloric LM-MP tissues after diabetes induction.

EXAMPLE 5

Chronic Diabetes Impairs Gastric nNOS Alpha Protein Dimerization in Female Gastric Tissue Since nNOSalpha protein expression and nitrergic relaxation are reduced in diabetic females, the changes in the dimerization state of nNOS alpha, known to be critical for the catalytic activity of the enzyme was investigated. The changes in the ratio of nNOS alpha dimers to monomers were examined using NH2-terminal antibody (derived from PDZ-GLGF domain) by low temperature SDS-PAGE. This assay is a convenient and reliable surrogate measure for the amount of stable dimer in vivo. As shown in FIG. 5D, the ratio of nNOS alpha dimer to monomer levels were significantly greater in healthy females compared to males in pyloric tissue. However, the ratio of nNOS alpha dimer to monomer levels was strikingly reduced in females on the onset of diabetes. Similar findings were noted in gastric fundus tissues. These findings suggested that the nNOS alpha dimerization and not total expression, played a critical role in modulating gastric motility functions in females. Hence, the present invention contemplates investigating the effects of diabetes and supplementation of BH4 on nNOS alpha dimerization, enzyme activity and NO production in the female gastric fundus, antrum and pyloric LM-MP tissues.

EXAMPLE 6

Chronic Diabetes Reduces NO Release in Gastric Tissues

Gastric LM-MPs were incubated for 24 hours in DMEM supplemented with 2% neurobasal medium (NB27) and 1% antibiotics. The concentration of NO (micromoles/mg tissue) was measured using readily available NO kit (Cayman corporation). As shown in FIG. 6, NO release was significantly reduced in diabetic gastric LM-MPs compared to female controls. These data suggested that decreased nNOSalpha dimerization was responsible for reduced NO release in female diabetic gastric tissues. The present invention contemplates examining whether supplementation of BH4 and female sex hormones restores reduced NO release in diabetic female gastric LM-MP tissues.

EXAMPLE 7

Chronic Diabetes Reduces BH4 Content in Gastric Pylorus Tissues

The concentration of tetrahydrobiopterin in female control and diabetic gastric pylorus tissues were measured using high performance liquid chromatography (HPLC). As shown in FIG. 7, significant ($p<0.05$) reduction in tetrahydrobiopterin content was seen in gastric tissues obtained from female diabetic rats. These studies suggested that nNOS alpha but not other proteins play a central role in the relaxation of the pyloric sphincter and circular smooth muscles in females. The present invention contemplates examining whether supplementation with BH4 and female sex hormones restores these effects.

EXAMPLE 8

Inhibition of BH4 Synthesis Reduces Nitrergic Relaxation in Gastric Tissue

Both nitrergic relaxation and nNOS alpha dimerization were decreased in gastric fundus of diabetic female rats compared to control group. Thus, whether the inhibition of endogenous tetrahydrobiopterin biosynthesis by DAHP (an inhibitor of GTPCH1) impaired the nitrergic function in the normal female gastric fundus was examined.

As shown in FIG. 8, in vitro incubation with the GTPCH1 inhibitor, DAHP (10 mM, 3 hours incubation), inhibited nitrergic relaxation in female control gastric tissues (n=2). Thus, the present invention contemplates examining whether in vivo supplementation of tetrahydrobiopterin restores nNOS dimerization, enzyme activity, NO production and thus, nitrergic function in the female diabetic gastric fundus, antrum and pylorus LM-MP tissues.

EXAMPLE 9

Inhibition of BH4 Synthesis Reduces nNOS Dimerization and no Release in Gastric Tissue The present invention examined whether treatment with DAHP in vitro uncoupled gastric nNOS dimerization and NO release in healthy female rats. Gastric longitudinal muscle-myenteric plexus (LM-MP) were incubated for 48 hours in the presence or absence of DHAP (10 mM). It was observed that inhibition of BH4 biosynthesis with DAHP decreased both nNOS dimerization (FIG. 9A) and NO release (FIG. 9B). These additional data further support the hypothesis that impaired biosynthesis of gastric BH4 accounts for the decrease in nNOS activity and nitrergic relaxation in female diabetic gastroparesis.

EXAMPLE 10

Chronic Diabetes Reduces GTPCH1 Expression in Female Gastric Tissues

GTPCH1 is the rate limiting enzyme in biopterin (BH4) synthesis. As shown in FIG. 10, GTPCH1 protein expression was significantly ($p<0.05$) decreased in stomachs of diabetic females (n=3). In a separate set of experiments, full thickness of gastric biopsies obtained from female patients with chronic diabetic gastroparesis was examined. Additionally, GTPCH1 mRNA levels, as measured by Affymetrix gene arrays, were substantially lower in gastric tissues of diabetic women than in controls (n=2, FIG. 11). Hence, the present invention contemplates investigating whether the GTPCH1 expression (mRNA and protein) and BH4 levels were altered in the female diabetic gastric fundus, antrum and pyloric LM-MP tissues.

EXAMPLE 11

BH4 Supplementation Improves Solid Gastric Emptying, nNOS Activity and Nitrergic Relaxation in Female Diabetic Gastric Fundal Tissues As shown in FIG. 12A, exogenous tetrahydrobiopterin (100 μM, 30 min incubation) increased nitrergic relaxation in diabetic (FD) but not control (FC) female stomachs (n=2, FIG. 12A). BH4 supplementation beginning from either day 1 (FIG. 12B) or 3 weeks (p=0.007) after diabetes induction significantly restored delayed gastric emptying for solids in female diabetic rats (FIG. 12C). Hence, tetrahydrobiopterin might play a critical role in NO mediated gastric motility and that a reduction in tetrahydrobiopterin synthesis might lead to gastric dysmotility in females. The present invention contemplates investigating whether oral supplementation of tetrahydrobiopterin or sepiapterin attenuate the impaired nNOS dimerization, enzyme activity, NO production and nitrergic relaxation in female diabetic gastric fundus, antrum and pylorus LM-MP tissues and restore the delayed gastric emptying in diabetic females.

EXAMPLE 12

Supplementation of Dietary BH4 Improves Intragastric Pressure, nNOSalpha Protein Expression in Female Diabetic Gastric Tissues Dietary BH4 (25 mg/kg b.w/rat/day) was supplemented for female rats for 12 weeks beginning from day 2 after diabetic induction. Intragastric pressure (IGP) was measured in female control, diabetic and diabetic+BH4 treated rats. As shown in FIG. 13A, supplementation of BH4 significantly attenuated increased IGP in diabetic female rats. In another experiment, diabetic females were treated for 3 weeks with BH4 and nNOS alpha protein expression was measured in treated and untreated gastric tissues. Diabetes, significantly decreased nNOSalpha protein expression and BH4 supplementation attenuated this (FIG. 13B). The above data strongly suggest that the gastric motility functions in females are primarily dependent on nitrergic mechanism and a decrease in BH4, a cofactor for nNOS function, may lead to altered IGP and delayed gastric emptying in diabetic females.

EXAMPLE 13

Estradiol-17Beta Delays Gastric Emptying for Solids in Healthy Females

Ovariectomized (OVX; removal of estrogen and progesterone) rats were treated either with estradiol-17beta ($E_2$) or progesterone ($P_4$) for three weeks and solid gastric emptying was assessed as reported previously. $E_2$ but not $P_4$ significantly delayed gastric emptying for solids in female rats (FIG. 14). These studies together with animal (Gangula et al., 2007) and clinical studies suggest that gastric emptying is slower in women compared to men and elevated levels of serum $E_2$ may play a critical role in this condition.

EXAMPLE 14

Estradiol-17Beta Accelerates Gastric Emptying for Solids in Chronic Diabetic Female Rats It has been demonstrated that sex steroid hormones, $E_2$ and $P_4$ are significantly reduced in STZ-induced diabetic rats and that $E_2$ treatment restored diabetes induced nephropathy in female rats. In the present invention, female rats were treated with $E_2$ for 3 weeks beginning from day 2 after diabetes induction. As shown in FIG. 2, diabetes significantly delayed gastric emptying for solids. Treatment with $E_2$, significantly restored delayed solid gastric emptying in diabetic female rats (FIG. 15). These data suggest that diabetes results in decrease in estrogen levels as reported earlier. Supplementation of exogenous estrogens accelerated the delayed gastric emptying in diabetic rats. The data from FIGS. 1 and 2 suggest that endogenous estrogens regulate gastric motility in both health and diabetic state.

EXAMPLE 15

Chronic Diabetes Reduces ER-Alpha Expression in Diabetic Female Gastric Tissues

Sex steroid hormones, $E_2$ and $P_4$ are significantly reduced in STZ-induced diabetic rats. Both estrogen receptor (ER) subtypes (alpha & beta) are primarily localized in myentric neurons of gastric in rats. Real time-PCR studies after normalizing with beta tubulin (neuronal marker) indicate that significant increases in ER-alpha mRNA were noticed in female control (FC) compared to male control (MC) group (FIG. 16). In addition, significant (p<0.05) reduction in ER-alpha mRNA was noticed in gastric tissues obtained from female but not male diabetic rats.

EXAMPLE 16

Estradiol-17Beta Restores Reduced nNOSalpha Protein Expression in Diabetic Female Rat Gastric Tissues As shown in FIG. 17, chronic diabetes reduced nNOSalpha protein expression in female rat gastric tissues. Further, it was shown for the first time that $E_2$ treatment, significantly restored nNOSalpha protein expression in diabetic female rat gastric tissues. The present invention contemplates examining whether $E_2$, $P_4$ or $E_2+P_4$ treatment restores impaired BH4 and nitrergic systems in diabetic female rat gastric tissues.

EXAMPLE 17

BH4 decreases the levels of TNF Alpha in Female Diabetic Rat Circulation

The level of TNF alpha in the circulation of diabetic female rat was examined after and before administration of tetrahydrobiopterin. It was observed that tetrahydrobiopterin decreased elevated TNF-alpha levels in the circulation of diabetic female rat. It is hypothesized that the elevated TNF-alpha might be involved in altering nitric oxide, free radical and NF-kB levels and causing gastroparesis in diabetic patients. The present invention contemplates examining the role of TNF alpha in diabetic gastroparesis.

EXAMPLE 18

Chronic Diabetes Decreases nNOS Activity, Nitrergic Relaxation, Expression of GTPCH1 and BH4 Content in the Female Rat Gastric Tissues The present invention contemplates examining whether diabetes alters nNOS expression, dimerization, nNOS activity, NO production and nitrergic relaxation in the female rat gastric fundus, antrum and pylorus LM-MPs. Briefly, diabetes is induced by streptozotocin injection (STZ, 55 mg/kg body weight) in female (7 week old) Sprague Dawley rats. Control groups receive vehicle only (citrate buffer, pH 4.0). Both control and diabetic rats are selected during the diestrous stage of the estrous cycle. Animals are sacrificed by decapitation after 12 weeks of diabetes. Gastric fundus, antrum and pylorus longitudinal muscle-myenteric plexus (LM-MP) tissues are collected, snap frozen and saved in −80° C. for biochemical analysis. nNOS mRNA is analyzed using Real-Time PCR. An optimal treatment regimen is determined for maximum nNOS expression in all regions of gastric LM-MP tissues in addition to NO levels. NH2-terminal polyclonal antibody derived from PDZ/GLGF motif (1-195 amino acids, Zymed Corporation, CA) is used to determine the active (dimers) and inactive (monomers) forms of nNOS alpha using low temperature SDS-PAGE in non-boiled samples. The COOH-terminal antibody is used for nNOS total protein expression.

The activity of nNOS from gastric LM-MPs is analyzed as the rate of conversion of L-(U-14C)-arginine to L-(U-14C)-citrulline. Nitrergic relaxation is assessed in gastric fundus, antrum and pylorus LM-MPs after transmural stimulation (electrical field stimulation, EFS) at various frequencies (1 Hz, 2 HZ, 5 Hz, 10 Hz) in vitro. NO dependent relaxation is confirmed by preincubating the tissues for 30 minutes with L-NAME ($10^{-4}$ M) or nNOS selective inhibitor (TRIM, $10^{-4}$M). In some experiments, the tissues are incubated for 30 minutes with tetrodotoxin (TTX, 1 µM) to determine whether nitrergic mediated relaxation is influenced by ENS. For examining the NO production, all regions of gastric LM-MPs are incubated in serum free neurobasal medium for 24 to 48 hours and media is collected for determination of total nitrites by a commercially available nitrite assay kit.

Additionally, whether chronic diabetes impairs the tetrahydrobiopterin biosynthetic pathway in female diabetic gastric fundus, antrum and pyloric LM-MPs is also examined herein. Briefly, the control and diabetic female rats (discussed supra) are sacrificed and their blood is collected to determine the levels of circulatory tetrahydrobiopterin and total biopterin (BH4, BH2, B). Gastric fundus, antrum and pyloric LM-MP tissues are collected, snap frozen and saved in −80° C. The GTPCH1 mRNA expression, the protein and the enzyme activity is measured by Real time RT-PCR, Western Blotting and HPLC, respectively. Additionally, the total biopterin (BH4, B2 and B) and ratio of total versus tetrahydrobiopterin content is measured by HPLC.

EXAMPLE 19

BH4 and/or Sepiapterin Supplementation Restores Impaired Gastric nNOS Alpha Dimerization, NO Synthesis and Nitrergic Relaxation in Diabetic Female Rat Gastric Tissues Dietary tetrahydrobiopterin or sepiapterin (2.5, 10 or 40 mg/day/Kg body weight) are administered to groups of diabetic female rats from day 1 until 12 weeks after diabetes induction by streptozotocin. The control group receive similar diet composition without tetrahydrobiopterin or sepiapterin. Tetrahydrobiopterin or sepiapterin (purchased from Swerick Laboratories, Switzerland) was compressed into rodent rat chow pellets (TestDiet, Land O'lakes, Purina Feed, LLC, Richmond, Ind.) without addition of water or heating to prevent oxidation of the compound. The concentration of tetrahydrobiopterin or sepiapterin in the pellets is calculated to provide a required dise (2.5, 10 or 40 mg) per kilogram body weight daily. Pellets are stored at −20° C. After the treatment periods, the total nNOS expression (mRNA, protein), nNOS alpha dimerization, enzyme activity and NO production in gastric fundus, antrum and pyloric LM-MPs is quantitated.

The effect of dietary tetrahydrobiopterin or sepiapterin on nitrergic relaxation is examined in all regions of female gastric tissues. Organ bath studies is performed herein. Nitrergic relaxation is demonstrated after transmural stimulation at various frequencies (1 Hz, 2 Hz, 5 Hz, 10 Hz) and NO-dependent relaxation is confirmed by preincubating gastric tissues with L-NAME (100 μM) or nNOS selective inhibitor (TRIM, 100 μM). Additionally, the GTPCH1 mRNA, protein, enzyme activity, BH4 content and total biopterins is measured. The BH4 and sepiapterin dose and time regimens is selected to mimic the endogenous concentration range.

The following references were cited herein:

Adeghate et al Cell Mol Life Sci 60, 1172-1179 (2003).
Alp et al., J clin Invest 112, 725-735 (2003)
Aytug et al., Am J Physiol Gastroenterol Liver Physiol 280, G255-G263 (2001)
Barros et al., Trends Mol Med 12:425-31 (2006).
Belai et al., Gastroenterology 89, 967-976 (1987).
Belai et al., Gastroenterology 92, 730-734 (1987).
Belai et al., Gastroenterology 98, 1427-1436 (1990).
Belai et al., Eur J Pharmacol 194, 225-234 (1991).
Belai et al., Gastroenterology 95, 1234-1241 (1988).
Bell et al., South Med J 95, 1297-1299 (2002).
Boonyaratanakornkit and Edwards, Semin Reprod Med 25:139-53 (2007).
Bityutsky et al., Am J Gastroenterol 92, 1501-1504 (1997).
Buchan A. M. Digestion 46 Suppl 2, 142-147 (1990).
Burnstock et al Clin Sci (Lond), 75, 629-635 (1988).
Camilleri M., Rev Gastroenterol Disord 2, 47-56 (2002).
Caruso et al., Neurochem Int (2007).
Cai et al., Cardiovasc Res 65, 838-849 (2005).
Cai et al., Diabetologia 48, 1933-1940 (2005).
Campbell-Thompson et al., J Endocrinol 171:65-73 (2001).
Cellek S., Curr Pharm Des, 10, 3683-3695 (2004).
Cellek S., Diabetes, 54, 212-219 (2005).
Cellek S., Diabetes, 52, 2353-2362 (2003).
Chen et al., Am J Physiol 268, G171-G176 (1995)
Cid et al., Ann N Y Acad Sci 2002; 966:143-57.
Coleski et al., J Pharmacol Exp Ther 312, 103-111 (2005).
Cosentino et al., Cardiovasc Res 43, 274-278 (1999).
Cosentino et al., Circulation 91, 139-144 (1995).
Coskun et al., Res Exp Med (Berl) 195, 49-54 (1995)
Di Giulio et al., J Neurosci Res 24, 355-361 (1989).
El-Sakka et al., Int J Impot Res 11:123-32 (1999).
Gangula et al., Am J Physiol Gastrointest Liver Physiol 292: G725-33 (2007).
Garcia-Duran et al., Circ Res 85:1020-6 (1999).
Gingerich and Krukoff, Endocrinology 146:2933-41 (2005).
Goren et al., Biochemistry 35, 16735-16745 (1996).
Gross and Levi., J Biol Chem 267, 25722-25729 (1992).
Heitzer et al., Diabetologia 43, 1435-1438 (2000).
Heitzer et al., Circ Res 86, E36-E41 (2000)
Huang et al., Cell 75, 1273-1286 (1993).
Huber et al., Am J. Physiol., 275, G1146-1156 (1998).
Ishiguchi et al., Am J Physiol Gastrointest Liver Physiol 279, G740-7 (2000).
Ishiguchi et al., Auton Neurosci 95, 112-120 (2002)
James et al Am J Physiol Gastrointest Liver Physiol 287, G612-619 (2004).
Jenkinson et al., Br J Pharmacol 116, 1535-1544 (1997).
Kamada et al., Brain Res Mol Brain Res 142, 19-27 (2005)
Kawano et al., Histochem Cell Biol 121:399-405 (2004).
Kim et al., J Pharmacol Sci 92 337-347 (2003).
Klatt et al., Embo J 14, 3687-3695 (1995).
Kobayashi et al., J Pharmacol exp Ther 256, 773-779 (1991)
Kone et al., Am J Physiol renal Physiol 285, F178-F190 (2003).
Knight et al., Am J Gastroenterol 92, 968-975 (1997)
Lam et al., Menopause 13:294-302 (2006).
Leonelli et al., Neuroscience 144:1293-304 (2007).
Maier et al., J Cardiovasc Pharmacol 35, 173-178 (2000)
Mankhey et al., Am J Physiol Renal Physiol 288:F399-405 (2005).
Mashimo et al., Gastroenterology, 119, 766-773 (2000).
Martinez-Cuesta et al., Br J Pharmacol 114, 919-924 (1995).
Meininger et al., FASEB J 18, 1900-1902 (2004)
Mitchell et al., Cardiovasc Pharmacol 43, 93-98 (2004)
Miyazaki-Akita et al., J Pharmacol Exp Ther 320:591-8 (2007).
Mizuta et al., Am J Physiol 277, G275-279 (1999).
Murphy and Steenbergen Heart Fail Rev 2007.
Nakamura et al., J Clin Invest 101, 1479-1489 (1998).
Nakao et al., J Physiol 507 (Pt. 2), 549-560 (1998).
Panda et al., J Biol chem, 278, 37122-37131 (2003).
Pannirselvam et al., Br J Pharmacol 29, 8-15 (1997)
Parkman et al., Gastroenterology 127, 1592-1622 (2004).
Patil et al., Indian J Exp Biol 43, 167-171 (2005).
Pieper M., J Cardiovasc Pharmacol 29, 8-15 (1997)
Putzke et al., Brain Res Mol Brain Res 85, 13-23 (2000)
Rayner and Horowitz, Nat Clin Pract Gastroenterol Hepatol 2, 454-462, (2005).
Resnick and Howard, Annu Rev Med 53:245-67 (2002).
Revicki et al., Qual Life Res 13, 833-844 (2004).
Saur et al., Gastroenterology 118, 849-858 (2000).
Saur et al., Am J Physiol Gastrointest Liver Physiol 282, G349-G358 (2002).
Scordalakes et al., J Comp Neurol 453:336-44 (2002).
Serova et al., Neuroscience 140:1253-63 (2006).
Serova et al., Brain Res 1015:1-8 (2004).
Shah et al., Am J Physiol regul Integr Comp Physiol, 279, R1478-1485 (2000).
Shang et al., Free Rad Biol Med 39, 1059-1074 (2005).
Simoncini et al., Hum Reprod (2007).
Soffer et al., Am J Gastroenterol 93, 1318-1323 (1998)
Stroes et al., J Clin Invest 99, 41-46 (1997)
Soykan et al., Dig Dis Sci 43, 2398-2404 (1998).
Takahashi T., J Gastroenterol 38, 421-430 (2003).
Takahashi et al., Gastroenterology 113, 1535-1544 (1997).
Thony et al., Biochem J 347 pt 1, 1-16 (2000).
Tougas et al., Gut 33, 466-471 (1992).
Undeland et al., Neurogastroenterol Motil 9, 19-24 (1997).
Undeland et al., Dig Dis Sci 41, 9-16 (1996).
Veiga et al., Neurosci Lett 402:150-3 (2006).
Wang et al., World J Gastroenterol 9:775-8 (2003).
Watkins et al J Clin Invest 106, 803 (2000)
Wen et al., Neuroreport 15:1515-8 (2004).
Widder et al., Hypertension 42:991-6 (2003).
Wrzos et al Dig Dis Sci 42, 2106-2110 (1997).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of restoring gut motility in an individual, suffering from gastroparesis comprising:

administering a pharmacologically effective amount of tetrahydrobiopterin or a derivative thereof, wherein said derivative is selected from the group consisting of 7,8-dihydrobiopterin and 6R-tetrahydrobiopterin, thereby restoring gut motility in the individual.

2. The method of claim 1, wherein said administration restores body weight, restores dimerization of neuronal nitric oxide synthase, activity of neuronal nitric oxide synthase, restores functions of monoamine neurotransmitters, lowers the level of reactive species, lowers the level of free radicals, suppresses stimulation of NF-κB, suppresses inflammatory signaling, lowers the level(s) of inflammatory cytokine(s) or a combination thereof.

3. The method of claim 2, wherein the inflammatory cytokine is TNF-α.

4. The method of claim 1, wherein the tetrahydrobiopterin or a derivative thereof is administered either alone or in combination with other medications.

5. A method of treating the gut-related disorder gastroparesis, in an individual, comprising:

administering a pharmacologically effective amount of tetrahydrobiopterin of or a derivative thereof, wherein said derivative is selected from the group consisting of 7,8-dihydrobiopterin and 6R-tetrahydrobiopterin, thereby restoring gut motility in the individual and treating the gastroparesis.

6. The method of claim 5, wherein the treatment of said disorder is due to restoration of intragastric pressure, improvement in gastric emptying, in symptoms of gastroparesis, in mast cell diversity and function and in blood flow, reduction of free radical induced-damage or free radical-induced apoptosis of neurons or other cellular components or a combination thereof in the individual.

* * * * *